United States Patent
Mishra et al.

(10) Patent No.: US 12,083,289 B2
(45) Date of Patent: Sep. 10, 2024

(54) MEDICAL DELIVERY SYSTEMS OF BIO-ABSORBABLE MATERIAL

(71) Applicant: Boston Scientific Medical Device Limited, Galway (IE)

(72) Inventors: Agrim Mishra, New Delhi (IN); Hitendra Purohit, Vadodara (IN); Deepak Kumar Sharma, Muzaffarnafar (IN); Subodh Morey, Ponda (IN); Nabarun Bhowmick, Kolkata (IN)

(73) Assignee: Boston Scientific Medical Device Limited, Galway (IE)

( * ) Notice: Subject to any disclaimer, the term of this patent is extended or adjusted under 35 U.S.C. 154(b) by 409 days.

(21) Appl. No.: 17/325,017

(22) Filed: May 19, 2021

(65) Prior Publication Data
US 2021/0361913 A1    Nov. 25, 2021

Related U.S. Application Data

(60) Provisional application No. 63/027,657, filed on May 20, 2020.

(51) Int. Cl.
*A61M 25/01* (2006.01)
*A61M 1/00* (2006.01)
(Continued)

(52) U.S. Cl.
CPC .......... *A61M 25/0147* (2013.01); *A61M 1/90* (2021.05); *A61M 25/0138* (2013.01);
(Continued)

(58) Field of Classification Search
CPC ............. A61M 37/0069; A61N 5/1027; A61N 2005/1011; A61N 2005/101
See application file for complete search history.

(56) References Cited

U.S. PATENT DOCUMENTS

| 5,281,197 A * | 1/1994 | Arias | A61M 37/0069 604/209 |
| 6,102,844 A * | 8/2000 | Ravins | A61M 37/0069 600/7 |

(Continued)

FOREIGN PATENT DOCUMENTS

| EP | 1114618 A2 * | 7/2001 | ....... A61B 17/00234 |
| EP | 1168976 B1 | 6/2009 | |

(Continued)

OTHER PUBLICATIONS

International Search Report and Written Opinion in International Application No. PCT/IB2021/054343, mailed Sep. 17, 2021 (12 pages).

*Primary Examiner* — Jason E Flick
*Assistant Examiner* — Adam J. Cermak
(74) *Attorney, Agent, or Firm* — Bookoff McAndrews, PLLC

(57) ABSTRACT

A medical device, for example a delivery catheter, may include a handle portion, a shaft portion extending distally from the handle portion, a deployment mechanism, and an actuation member positioned on the handle portion. The shaft portion may include a working channel and a distal tip portion having a payload chamber configured to receive a payload, such as a bio-absorbable foam. The distal tip portion may be operatively connected to the working channel. The deployment mechanism may be positioned in the working channel, and may be operable to deploy the payload out from the distal tip portion. The actuation member may be actuatable to operate the deployment mechanism.

20 Claims, 14 Drawing Sheets

(51) Int. Cl.
 *A61M 25/09* (2006.01)
 *A61M 37/00* (2006.01)
(52) U.S. Cl.
 CPC ........ *A61M 25/09* (2013.01); *A61M 37/0069* (2013.01); *A61M 25/0136* (2013.01)

(56) References Cited

U.S. PATENT DOCUMENTS

| | | | | |
|---|---|---|---|---|
| 6,197,324 B1* | 3/2001 | Crittenden | ............ | A61K 31/00 |
| | | | | 424/423 |
| 6,338,345 B1* | 1/2002 | Johnson | ............ | A61B 17/1219 |
| | | | | 600/114 |
| 6,530,875 B1* | 3/2003 | Taylor | ............ | A61M 37/0069 |
| | | | | 600/7 |
| 7,150,709 B1* | 12/2006 | Schmidt | ............ | A61N 5/1007 |
| | | | | 600/7 |
| 7,185,657 B1* | 3/2007 | Johnson | ............ | A61B 17/3468 |
| | | | | 128/898 |
| 7,335,155 B2* | 2/2008 | Chu | ............ | A61M 37/0069 |
| | | | | 600/7 |
| 7,972,295 B2* | 7/2011 | Freyman | ............ | A61M 37/0069 |
| | | | | 604/57 |
| 8,080,032 B2* | 12/2011 | van der Burg | ... | A61B 17/12136 |
| | | | | 606/200 |
| 8,357,169 B2* | 1/2013 | Henniges | ............ | A61B 17/8816 |
| | | | | 606/92 |
| 8,670,818 B2* | 3/2014 | Ranpura | ............ | A61B 90/39 |
| | | | | 600/431 |
| 9,327,061 B2* | 5/2016 | Govil | ............ | A61L 27/54 |
| 9,403,033 B1* | 8/2016 | Brachman | ............ | A61N 5/1007 |
| 9,579,077 B2* | 2/2017 | Casanova | ............ | A61B 90/39 |
| 9,999,758 B2* | 6/2018 | Vetter | ............ | A61B 17/3468 |
| 10,076,335 B2* | 9/2018 | Zaver | ............ | A61B 17/12172 |
| 10,888,710 B1* | 1/2021 | Brachman | ............ | A61N 5/1007 |
| 11,446,059 B2* | 9/2022 | Morey | ............ | A61B 17/0482 |
| 2002/0026147 A1* | 2/2002 | Fontayne | ............ | A61N 5/1007 |
| | | | | 604/118 |
| 2004/0097780 A1* | 5/2004 | Otsuka | ............ | A61M 37/0069 |
| | | | | 600/7 |
| 2004/0122351 A1* | 6/2004 | Hamazaki | ............ | A61N 5/1007 |
| | | | | 600/7 |
| 2004/0147800 A1* | 7/2004 | Barber | ............ | A61N 5/1007 |
| | | | | 600/7 |
| 2005/0035310 A1* | 2/2005 | Drobnik | ............ | G21G 4/00 |
| | | | | 600/7 |
| 2007/0219612 A1* | 9/2007 | Andreas | ............ | A61B 17/12022 |
| | | | | 623/1.11 |
| 2008/0033280 A1* | 2/2008 | Lubock | ............ | A61B 17/3468 |
| | | | | 600/414 |
| 2009/0069625 A1* | 3/2009 | Helle | ............ | A61N 5/1007 |
| | | | | 600/7 |
| 2013/0006101 A1* | 1/2013 | McHugo | ............ | A61B 90/39 |
| | | | | 600/432 |
| 2013/0131434 A1* | 5/2013 | Nakaji | ............ | A61N 5/1007 |
| | | | | 600/8 |
| 2014/0371586 A1* | 12/2014 | Ryan | ............ | A61B 90/39 |
| | | | | 600/431 |
| 2016/0129221 A1* | 5/2016 | Haverkost | ............ | A61M 25/0068 |
| | | | | 604/524 |
| 2016/0324616 A1* | 11/2016 | Zenz-Olson | ............ | A61F 2/0805 |
| 2020/0113599 A1* | 4/2020 | Morey | ............ | A61B 17/0469 |
| 2021/0187190 A1* | 6/2021 | Congdon | ............ | A61M 5/31586 |
| 2021/0228905 A1* | 7/2021 | Brachman | ............ | A61N 5/1007 |
| 2021/0236778 A1* | 8/2021 | Kim | ............ | A61K 51/1255 |
| 2021/0361342 A1* | 11/2021 | Sharma | ............ | A61M 1/96 |

FOREIGN PATENT DOCUMENTS

| | | |
|---|---|---|
| WO | 9722379 A2 | 6/1997 |
| WO | 2016044226 A2 | 3/2016 |

* cited by examiner

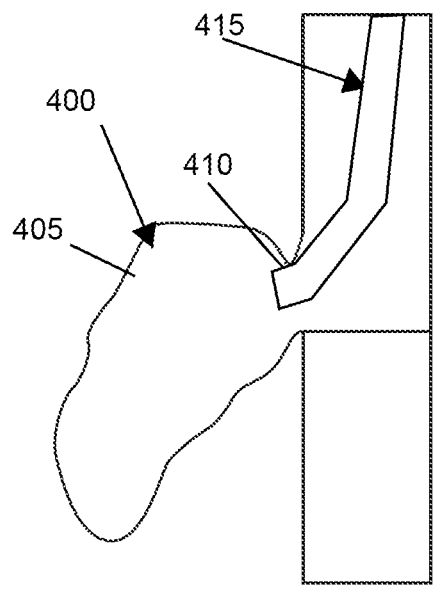
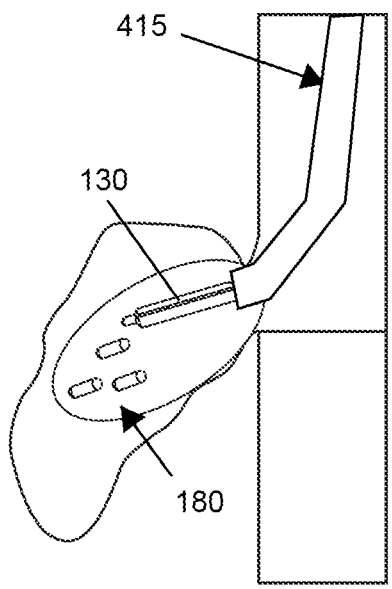
FIG. 7A  FIG. 7B
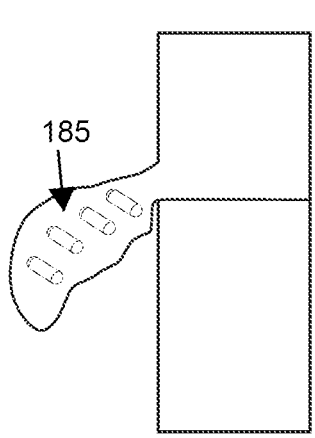
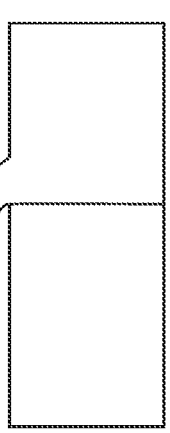
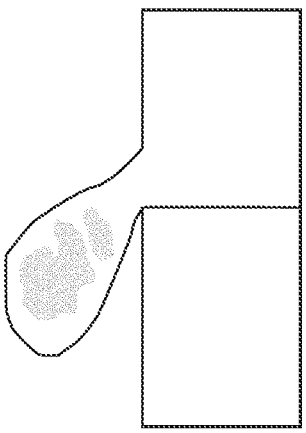
FIG. 7C  FIG. 7D  FIG. 7E

MEDICAL DELIVERY SYSTEMS OF BIO-ABSORBABLE MATERIAL

CROSS-REFERENCE TO RELATED APPLICATIONS

This application claims the benefit of priority from U.S. Provisional Application No. 63/027,657, filed on May 20, 2020, which is incorporated by reference herein in its entirety.

TECHNICAL FIELD

Various aspects of the disclosure relate generally to medical delivery systems, devices, and related methods. Examples of the disclosure relate to systems, devices, and related methods for delivering bio-absorbable material for absorbing fluid present in a wound or cyst, such as in the GI tract, bile ducts, pancreas, and others, among other aspects.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Perforations, wounds, or cysts also may arise separately from procedures. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

SUMMARY

Aspects of the disclosure relate to, among other things, systems, devices, and methods for treating a target treatment site using a delivery catheter to deliver bio-absorbable material for absorbing fluid from a wound or cyst, among other aspects. Each of the aspects disclosed herein may include one or more of the features described in connection with any of the other disclosed aspects.

According to an example, a medical device may include a handle portion, a shaft portion extending distally from the handle portion, a deployment mechanism, and an actuation member positioned on the handle portion. The shaft portion may include a working channel and a distal tip portion having a payload chamber configured to receive a payload, such as a bio-absorbable foam. The distal tip portion may be operatively connected to the working channel. The deployment mechanism may be positioned in the working channel, and may be operable to deploy the payload out from the distal tip portion. The actuation member may be actuatable to operate the deployment mechanism.

Any of the medical devices described herein may include one or more of the following features. The distal tip portion defines a slit extending through a wall of the distal tip portion, wherein the slit is configured to enable the distal tip portion to flex in order to receive and deploy the payload. The shaft portion further includes: a pair of fluid channels configured to selectively pass fluid and negative pressure there-through. The shaft portion further includes a guide channel is configured to pass a guide wire there-through. The shaft portion further includes a slit that extends through a side-wall of the shaft portion to the guide channel and along a length of at least a portion of the shaft portion, and that is configured to pass at least a portion of a length of the guide wire there-through. The distal tip portion further includes a pair of distal fluid openings operatively connected to the pair of fluid channels. The distal tip portion further a distal guide wire opening operatively connected to the guide channel. The handle portion includes a fluid connection that is in fluid communication with the pair of fluid channels, and that is configured to connect with at least one of a source of negative pressure or a source of delivery fluid. The payload includes a plurality of capsules. An inner surface of the payload chamber defines a plurality of cavities for receiving each of the respective plurality of capsules. The distal tip portion defines a slit between the working channel and an outer surface of the distal tip portion, and wherein the actuation of the actuation member causes the slit to expand. The distal tip portion is a separate piece from the shaft portion. The distal tip portion is configured to couple with a distal end of the shaft portion. The distal tip portion is preloaded with the payload prior to coupling with the distal end of the shaft. The medical device further includes a coupling member. The coupling member includes: a first end configured to couple directly with the distal end of the shaft portion; a second end opposite the first end configured to couple directly with a proximal end of the distal tip portion in order to couple the distal tip portion to the tubular portion; and at least one alignment element configured to align the shaft portion with the distal tip portion. The shaft portion further includes a cautery lumen. The handle portion includes a cautery connector configured to operatively couple the cautery lumen to a cautery device. The distal tip portion further includes a cautery element positioned on an outer surface of the distal tip portion. The deployment mechanism includes: a pull wire; and a plunger positioned at a distal tip of the pull wire. The actuation member includes a roller knob operatively engaged with a proximal end of the pull wire. The deployment mechanism includes a pressure channel configured to provide a positive pressure from a pressure source to the payload in order to deploy the payload. The deployment mechanism includes a grasper mechanism that is operatively connected to the actuation member, and that includes two arms that are operable to selectively hold and release the payload. The handle portion includes a connection member configured to removably couple the medical device to a scope device. The distal tip portion further includes at least one echogenic marking positioned on an outer surface of the distal tip portion.

According to another example, a medical device may include a delivery catheter and a cartridge. The delivery catheter may include a handle portion, a shaft portion extending distally from the handle portion, a deployment mechanism, and an actuation member positioned on the handle portion. The shaft portion may include a working channel and a distal tip portion having a payload chamber configured to receive a payload, and operatively connected to the working channel. The deployment mechanism may be positioned in the working channel, and operable to deploy the payload out from the distal tip portion. The actuation member may be actuatable to operate the deployment mechanism. The cartridge may include an opening into an interior of the cartridge configured to receive the distal tip portion of the delivery catheter, and a bio-absorbable foam payload positioned in the interior and arranged such that the casing is configured to load the distal tip portion with the payload in response to the distal tip portion being advanced into the casing via the opening.

Any of the medical devices described herein may include one or more of the following features. The cartridge includes two half-shells coupled together. At least one of the two half-shells is at least partially transparent, such that the payload is visible there-through. At least one of the two half shells include a payload channel that extends from the opening and that is configured to receive the distal tip portion. The payload is positioned in the payload channel. The payload includes a plurality of individual capsules. The plurality of individual capsules has a spherical or ovoid shape.

According to a further example, a delivery catheter may include a handle portion at a proximate end of the delivery catheter, a shaft portion extending distally from the handle portion, a deployment mechanism, and an actuation member positioned on the handle portion. The shaft portion may include a distal tip portion including a payload chamber configured to receive a bio-absorbable foam payload, and a working channel operatively connected to the payload chamber. The deployment mechanism may be positioned in the working channel and operable to deploy the payload out from the distal tip portion. The actuation member may be actuatable to operate the deployment mechanism. The distal tip portion may further include a slit extending through a side-wall of the working channel, the slit sized and configured to enable the distal tip portion to flex in response to operation of the deployment mechanism in order to receive and deploy the payload. The payload may be a plurality of capsules. An interior surface of the payload chamber may be shaped so as to define a respective cavity for each of the capsules, the respective cavity shaped so as to provide tactile feedback of actuation of each of the individual capsules to the actuation member.

According to another example, a delivery device may be used to deliver a payload to a target treatment site within a body. A method of using the delivery device to deliver the payload may include introducing a shaft portion of the delivery device into a proximal end of a scope device with a distal end located at the target treatment site. The shaft portion of the delivery device may be advanced such that a distal tip portion of the delivery device is advanced out from the scope device and into the target treatment site. An actuation member positioned on a proximal handle portion of the delivery device may be actuated. The actuation member may be configured to operate a deployment mechanism positioned in a working channel of the delivery device. The working channel of the delivery device may be operatively connected to the distal tip portion. The distal tip portion may include a payload chamber having a payload. The deployment mechanism may be operable to deploy the payload out from the payload chamber, such that the actuating of the actuation member deploys the payload into the target treatment site It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIGS. 7A-7H depict the delivery catheter of FIG. 1 in use.

DETAILED DESCRIPTION

Figure 1:
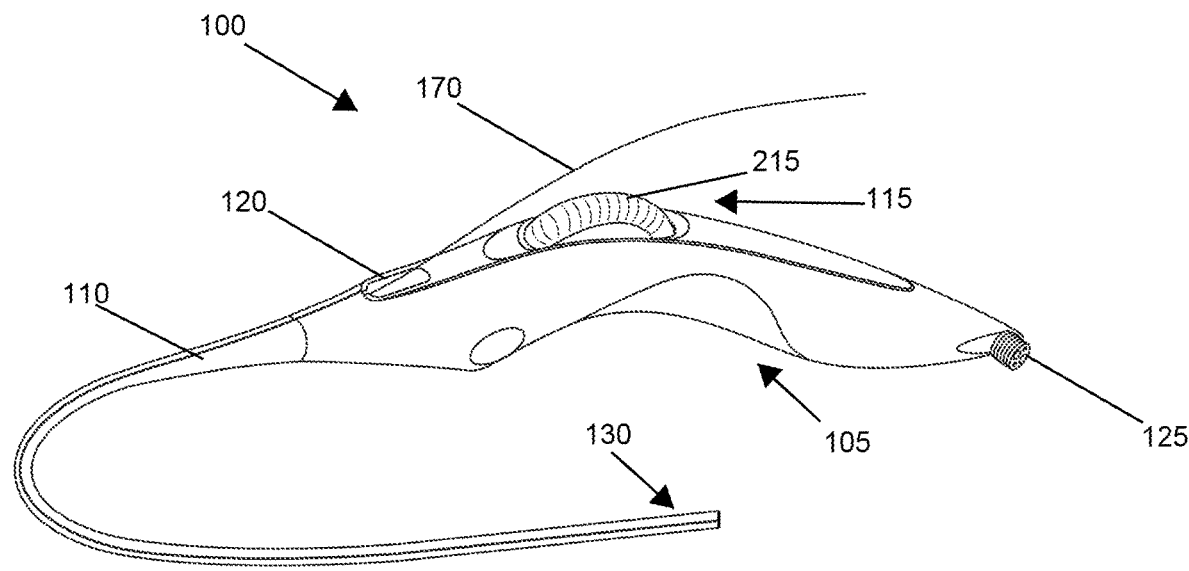
FIG. 1 is a perspective view of an exemplary delivery catheter for delivering material.

Treatments for wounds or cysts in a GI tract, bile ducts, pancreas, and other locations of a subject's body have been proposed. However, conventional treatments may be invasive, complex, or uncomfortable for a patient, and may require frequent follow-up or surveillance. Thus, there is a need for a less medically-invasive treatment option. There is also a need for a treatment option that requires less or less-frequent post-procedure surveillance. Further, there is a need for a treatment option that is adaptable for use at various locations within the body, and that is adapted for safe and controlled use.

Examples of the disclosure include systems, devices, and methods for treating a wound or cyst within the body with a material such as bio-absorbable foam. In examples, in a procedure for treating a wound or cyst within the body, e.g. in the GI tract, bile ducts, pancreas, and/or other locations generally accessible via a scope device (e.g., endoscope, laparoscope, bronchoscope, colonoscope, ureteroscope, duodenoscope, endoscopic ultrasound scope), the scope device may be advanced into the body and to a site of the wound or cyst. A delivery device (including, e.g., a catheter) may be advanced through a working channel of the scope device so that a distal tip portion of the delivery device protrudes distally from the scope device. An actuation member of the delivery device may be actuated to operate a deployment mechanism to deploy a payload of material, such as bio-absorbable foam, from the distal tip portion and to the site of the wound or cyst.

Reference will now be made in detail to aspects of the disclosure, examples of which are illustrated in the accompanying drawings. Wherever possible, the same or similar reference numbers will be used through the drawings to refer to the same or like parts. The term "distal" refers to a direction away from an operator, and the term "proximal" refers to a direction toward an operator. The terms, "channel," "lumen," and the like generally encompass a passage for conveying material and/or an operative connection through an element. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Unless expressly stated otherwise, the examples described herein may include single-use/disposable medical devices or reusable medical devices.

FIG. 1 shows an exemplary delivery device 100 in accordance with an example of this disclosure. The delivery device 100 may include a proximal handle portion 105 and a shaft 110 that extends distally from the handle portion 105. The handle portion 105 may have an ergonomic shape configured to be gripped by a hand of an operator. The handle portion 105 may include an actuation member 115, a guide wire inlet 120, and a fluid connector 125, each of which will be described in further detail below. The handle portion 105 may be formed from any suitable material (e.g., plastic).

A distal tip of a distal end portion 130 of the shaft 110 may taper distally. The taper of the distal end portion 130 of the delivery device 100 may facilitate an atraumatic entry of the delivery device 100 into body lumen of a subject and/or a treatment site. The shaft 110 may define a plurality of channels (e.g., a working channel 135, a guide wire channel 140, and two fluid channels 145) that are operatively and/or fluidly connected to one or more of the actuation member 115, the guide wire inlet 120, and/or the fluid connector 125. The channels may extend through a length of the shaft 110 to the distal end portion 130, as discussed in further detail below. Distal tip 130 may be more rigid than more proximal portions of shaft 110.

The shaft 110 may be formed from any acceptable flexible material such as, Polytetrafluoroethylene (PTFE), ethylene tetrafluoroethylene (ETFE), fluorinated ethylene propylene (FEP), polyoxymethylene (POM), ethylene tetrafluoroethylene (ETFE), fluorinated ethylene propylene (FEP), polyoxymethylene (POM), polyether block ester, polyurethane, polypropylene (PP), polyvinylchloride (PVC), polyetherester, ether or ester based copolymers (for example, butylene/poly(alkylene ether) phthalate and/or other polyester elastomers, polyamide, elastomeric polyamides, block polyamide/ethers, polyether block amide (PEBA), ethylene vinyl acetate copolymers (EVA), silicones, polyethylene (PE), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro (propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. A material of shaft 110 may minimize kinking while allowing flexibility.

The shaft 110 may include a coating such as, for example, a lubricious, a hydrophilic, a protective, or other type of coating. Lubricious coatings may improve steerability and improve lesion-crossing capability. Hydrophilic coatings may improve the passability of the shaft 110 in a working channel of a scope device and/or through stringent anatomical curvatures, as discussed in further detail below. Some examples of suitable coating materials may include silicone and the like, hydrophilic polymers, such as high-density polyethylene (HDPE), PTFE, polyarylene oxides, polyvinylpyrolidones, polyvinylalcohols, hydroxy alkyl cellulosics, algins, saccharides, caprolactones, and the like, and mixtures and combinations thereof. Some coating polymers may be blended together or with formulated amounts of water insoluble compounds (including some polymers) to yield coatings with suitable lubricity, bonding, and solubility.

Figure 2:
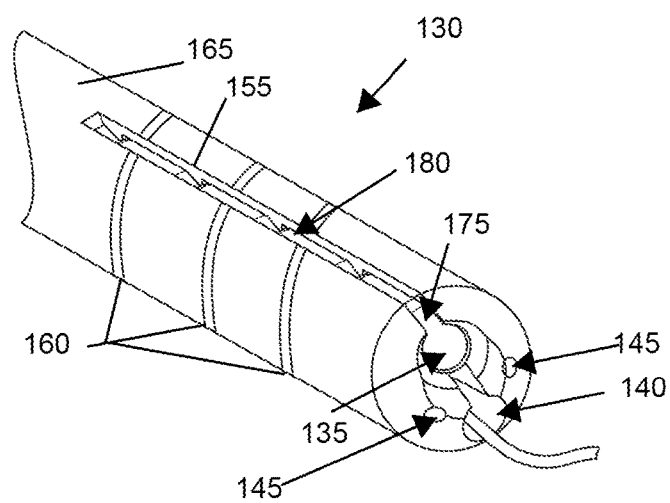
FIG. 2 is a perspective view of a distal tip portion of the delivery catheter of FIG. 1.
Figure 3:
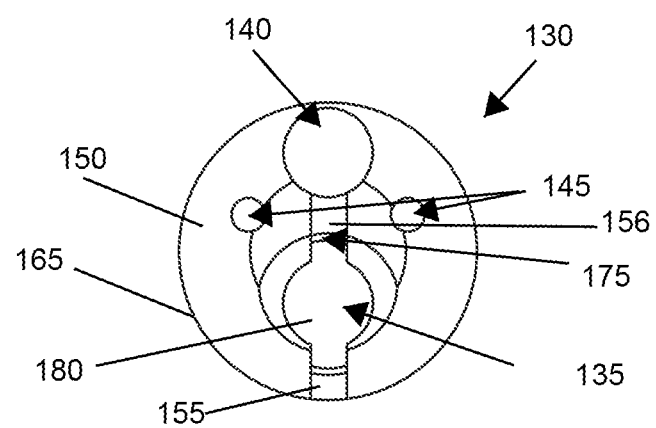
FIG. 3 is an end view of the distal tip portion of the delivery catheter of FIG. 1.

FIGS. 2 and 3 show a perspective view and an end view, respectively, of the distal end portion 130 of the shaft 110 from FIG. 1. The shaft 110 may define the working channel 135, the guide wire channel 140, and the pair of fluid channels 145. For example, the shaft 110 may include extruded tubing that defines four lumens—the working channel 135, the guide wire channel 140, and the two fluid channels 145. The working channel 135, the guide wire channel 140, and the pair of fluid channels 145 may each extend from a proximal end of shaft 110, through a length of shaft 110, to distal end portion 130.

The working channel 135, the guide wire channel 140, and the pair of fluid channels 145 may terminate in distal openings on a distal face 150 of the distal tip portion 130. Distal openings of the working channel 135 and the guide wire channel 140 may be aligned along a diameter of the distal face 150 of the shaft 110. The pair of fluid channels 145 may be disposed symmetrically about the diameter along which the distal openings of the working channel 135 and the guide wire channel 140 are disposed. Any suitable arrangement of the various channels may be used in other examples. Although two fluid channels 145 are shown, it will be appreciated that any suitable number of fluid channels 145 may be utilized (e.g., one fluid channel 145 or more than two fluid channels 145).

Distal end portion 130 may define a first slit 155. The first slit 155 may extend along a longitudinal axis of the shaft 110. The first slit 155 may extend along only a portion of the distal end portion 130 (e.g., a distal most portion). The first slit 155 may extend through an outer wall of the distal end portion 130, between an outer surface 165 of distal end portion 130 and the working channel 135. The first slit 155 may be sized and/or configured to enable the shaft 110 to flex in order to receive and/or deploy a payload, as discussed in further detail below.

The distal end portion 130 may also define a second slit 156 (see FIG. 3). The second slit 156 may extend through a wall of the distal end portion 130 between the working channel 135 and the guide wire channel 140. The second slit 156 may extend proximally from distal face 150 along a longitudinal axis of the distal end portion 130. The second slit 156 may extend along less than an entire length of the distal end portion 130. The second slit 156 may be a same length as the first slit 155 along the longitudinal axis. The second slit 156 may be configured to, along with first slit 155, enable shaft 110 to flex while receiving or deploying a payload, as discussed below. The first slit 155 and the second slit 156 may lie along the same diameter of the distal end portion 130, so that the first slit 155 is aligned with the second slit 156.

Distal end portion 130 may also include one or more echogenic markings 160 to facilitate visualization of distal end portion 130. The echogenic marking 160 may include any suitable echogenic marking such as, for example, a dimple, groove, or the like, and/or may include any acceptable material such as, for example, powdered tantalum, tungsten, barium carbonate, bismuth oxide, barium sulfate or other barium- or bismuth-containing compounds. The echogenic marking 160 may include echogenic material inserted into and/or impregnated into the outer wall of the housing 150 or on an outer surface 165 of the distal end portion 130. The echogenic marking 160 may additionally or alternatively include a structure formed in the outer wall of the distal end portion 130. As shown in FIG. 2, the distal tip portion 130 may include three echogenic markings 160. Any suitable number of echogenic markings may be included. As discussed in further detail below, the echogenic marking 160 may be used to locate and/or orient the distal tip portion 130 of the delivery device 100 during a procedure to deploy material, such as bio-absorbable foam, to a treatment site.

With reference to FIGS. 1-3, the guide wire channel 140 may be in communication with the guide wire inlet 120. The guide wire inlet 120 and the guide wire channel 140 may be configured to receive and pass a guide wire 170 in order to guide advancement of the delivery device 100 along a working channel of a scope device. For example, a proximal end of the guide wire 170 may be inserted into a distal end of the working channel 135, and the delivery device 100 may be guided along the guide wire 170 toward a target site. The proximal end of the guide wire 170 may protrude out from the guide wire inlet 120 due to the advancement of the delivery device 100. Any suitable guide wire 170 may be used with the delivery device 100.

The pair of fluid channels 145 may be in fluid communication with the fluid connector 125. For example, one or more channels (not shown) may extend from the connector 125, through the handle portion 105, and to proximal ends of the pair of fluid channels 145. The fluid connector 125 may be configured to interface with at least one of a source of negative pressure (e.g., suction) or a source of fluid (e.g., air, water, or a medically active agent). The fluid connector 125 may include, for example, a luer connection for connecting handle portion 105 to a source of suction or fluid. Sources of suction may include, for example, a syringe or a compressor. Fluids may pass between the distal end portion 130 and the fluid connector 125 via the fluid channels 145.

As discussed in further detail below, in some examples, a source of negative pressure may be coupled to fluid connector 125 and may be operative to remove fluid (e.g., body fluids or fluids delivered from a scope) from the treatment site, via the distal openings of fluid channels 145. Although other examples may include any number of fluid channels 145, or no fluid lumens, it has been found that two fluid channels 145 (as shown in FIGS. 2 and 3) may be sized and configured to pass a desired amount of fluid proximally while maintaining a desired amount of negative pressure. Alternatively, a source of fluid (e.g., air, water, dye, or contrast) may be coupled to fluid connector 125 in order to provide fluid out of the distal openings of fluid channels 145. In a single procedure, fluid channels 145 may be used for different functions. For example, a suction source or a fluid source may be coupled to fluid connector 125 at different times. Alternatively, handle portion 105 may include additional fluid connectors 125, which may be in communication with different fluid channels 145, so that both suction and other fluids (e.g., air/water) may be provided via the respective fluid channels 145.

A distal portion of the working channel 135 may form a payload chamber 175 configured to receive a payload 180. Payload 180 may include bio-absorbable foam, which may be deployed by the delivery device 100 at the treatment site. Alternatively or additionally, the payload 180 may include alternative materials, such as treatment materials (e.g., medicated material). The delivery device 100 is not limited to use with any one type of payload 180 and may be used with a variety of materials, as described below. Slits 155 and 156 may extend the length of the payload chamber 175 to facilitate flexing, as described below.

Figure 4:
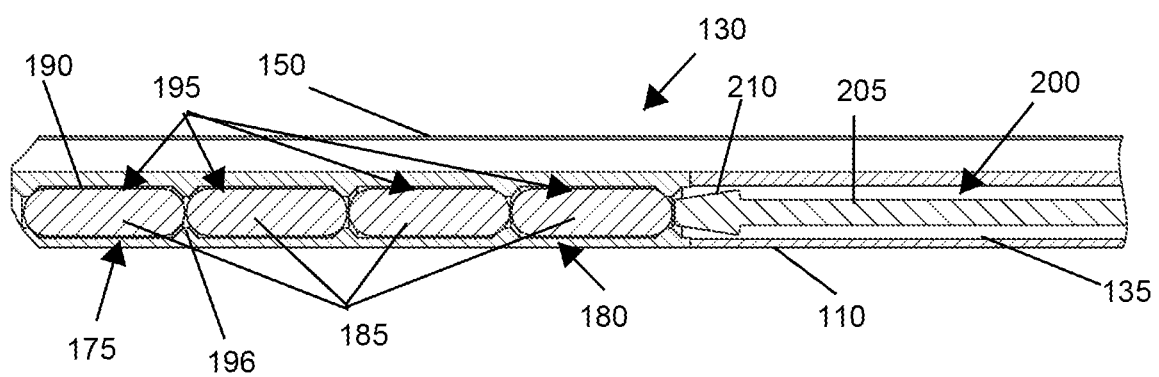
FIG. 4 is a side cross section view of the distal tip portion of the delivery catheter of FIG. 1.

FIG. 4 depicts a cross section view of distal tip portion 130. As shown in FIG. 4, the payload 180 may include a plurality of individual capsules 185. The payload chamber 175 may have an inner surface 190 that is shaped so as to define a respective cavity 195 for each of the plurality of individual capsules 185. The inner surface 190 may define a plurality of circumferential ribs 196 that extend into payload chamber 195. The inner surface, including ribs 196, may define cavities 195 that have shapes that substantially correspond with a shape of the individual capsules 185. The ribs 196 may be longitudinally spaced from one another such that one capsule 185 may fit between two adjacent ribs 196. Each of the cavities 195 may be shaped so as to hold and/or retain individual capsules 185 therein prior to deployment, as discussed in further detail below. A number of cavities 195 may correspond to a maximum number of capsules 185 to be loaded into delivery device 100 and delivered to the treatment site. Some of the cavities 195 may not be utilized during a procedure and may remain empty. For example, one or more of the cavities 195 on a proximal end of the chamber 175 may remain empty. As shown in FIG. 4, the payload chamber 175 may include four cavities 195 for receiving a maximum of four capsules 185. Alternatively, the payload chamber may include any number of cavities for receiving any number of capsules.

A deployment mechanism 200 may be positioned in the working channel 135 of the shaft 110. The deployment mechanism 200 may be operatively connected to the actuation member 115. The deployment mechanism may extend distally from actuation member 115, through working channel 135, toward chamber 175. Deployment mechanism 200 may be operable, via the actuation member 115, to deploy the payload 180 (comprising capsules 185) out from the distal opening of working channel 135.

The deployment mechanism 200 may include a pull wire 205 and a plunger 210 positioned at a distal end of the pull wire 205. The plunger 210 and the pull wire 205 may be separate components coupled to one another or may be one single, unitary piece of material. The pull wire 205 may be coupled to actuation member 115. Any acceptable type of operative engagement between the actuation member 115 and the pull wire 205 may be used such as, for example, a rack and pinion, a gear, a spool, or other suitable mechanisms. Actuation member 115 may include a rotatable wheel 215. An axis of the rotatable wheel 215 may be perpendicular to a longitudinal axis of the delivery device 100. Rotation of the rotatable wheel 215 may cause the pull wire 205, and therefore the plunger 210, to be moved proximally or distally. For example, rotation of the rotatable wheel 215 in a distal direction may cause advancement (distal movement) of the pull wire 205 and, in turn, the plunger 210. Proximal rotation of the rotatable wheel 215 may cause retraction (proximal movement) of the wire 205 and, in turn, the plunger 210. Rotatable wheel 215 may allow precise actuation to deploy only a desired amount of payload 180. The rotatable wheel 215 is merely exemplary. The actuation member 115 may additionally or alternatively include any suitable mechanisms (e.g., knobs, levers, rotatable wheels, sliders, or switches) that may be used to move the plunger 210 proximally and/or distally.

As the pull wire 205 and the plunger 210 are moved distally, the plunger 210 may exert a distal force on the payload 180, along a longitudinal axis of the delivery device 100, toward the distal opening of working channel 135. As described below, the plunger 210 may distally advance to push one or more of the capsules 185 of payload 180 out of the distal opening of working channel 135.

A configuration of the plunger 210, alone or in conjunction with a shape of the capsules 185, may be configured to provide the tactile feedback to a user. For example, a maximum diameter of capsules the 185 may be greater than a diameter of the chamber 175 at the ribs 196. Therefore, as the plunger 210 pushes the capsule 185 against the rib 196, an amount of force may be required on the rotatable wheel 115 to cause the shaft 110 to flex via the first slit 155 and the second slit 156. The first slit 155 and the second slit 156 may widen or expand as the shaft 110 flexes. As the shaft 110 flexes, the chamber 175 may increase in diameter, allowing for the capsule 185 to pass by the rib 196. After the shaft 110 flexes, a lesser force on the rotatable wheel 115 may be required to continue advancing the plunger 210. The differential in force required on the rotatable wheel 215 before and following flex of the shaft 110 may provide tactile feedback to the user. Additionally or alternatively, the capsules 185 may be compressible so that, when sufficient force is exerted on capsules 185, capsules 185 may compress to pass ribs 196, thereby providing similar tactile feedback.

As shown in FIG. 4, the plunger 210 may have a tapered shape that has a larger diameter at a proximal end than at a distal end of plunger 210. A portion of the plunger 210 (e.g., the proximal end of the plunger 210) may have a diameter that is larger than a diameter of the chamber 175 at each rib 196. In order for the plunger 210 to pass one of the ribs 196, the shaft 110 may flex via the first slit 155 and/or the second slit 156, providing tactile feedback to the user as explained above.

Additionally or alternatively, the plunger 210 may be formed from a material that is resiliently flexible and/or compressible. As the plunger 210 encounters the rib 196 forming a proximal or distal end of one of the cavities 195, the rib 196 may exert a radially inward force on the plunger 210 sufficient to compress plunger 210, thereby allowing the plunger 210 to pass the ribs 196. The plunger 210 may be configured to only allow one-way, distal movement of the plunger 210 past the ribs 196. For example, a tapered shape of the plunger 210 may allow distal movement of the plunger 210 past the ribs 196 but not proximal movement of the plunger 210. Alternatively, a middle portion of the plunger 210 may have a widest diameter, and the plunger 210 may be tapered inward in both proximal and distal directions, to allow bi-directional movement of the plunger 210 past the ribs 196. Alternatively, an entirety of the plunger 210 may have a diameter smaller than a diameter of the chamber 175 at the ribs 196. Alternatively, the plunger may have any suitable shape such as, for example, a spherical shape, a rounded shape, a tubular shape, or a rectilinear shape.

As discussed above, the payload 180 may include a plurality of individual capsules 185. Each capsule 185 may be bio-absorbable, and may include a bio-absorbable foam configured to assist the body in absorbing fluid that may be present at the treatment site. For example, the bio-absorbable foam may be configured to absorb fluid at the treatment site until the bio-absorbable foam has been absorbed by the body. Each capsule 185 may be a gelatin-based bio-absorbable cartridge that is filled with the bio-absorbable foam. The bio-absorbable foam within the capsule 185 may be in the form of a foaming agent, a powder, a particulate form, or the like. The payload 180 may further include or be coated with a material such as, for example, a bio-active or chemotherapeutic agent, a dye or contrast agent, or the like. The material may be mixed or impregnated into the material of capsules 185 (e.g., the bio-absorbable foam). The materials may function to, for example, reduce a mucinous cyst and/or inhibit formation of cancerous tissue. Alternatively, the payload 180 (formed of, e.g., capsules 185) may include any other suitable substance desired to be delivered to a subject's body.

A payload chamber 175 that is devoid of a payload 180 (e.g., prior to a first use or following deployment of an initial payload 180) may be loaded or reloaded with the deployment mechanism 200 in a retracted position, e.g., the position depicted in FIG. 4. In other words, when the pull wire 205 and plunger 210 are not occupying the payload chamber 175, the payload 180 may be loaded into the payload chamber 175 from the distal end of the delivery device 100. Alternatively or additionally, the payload chamber may be pre-loaded with the payload 180 prior to a first use of the delivery device 100.

Figure 5:
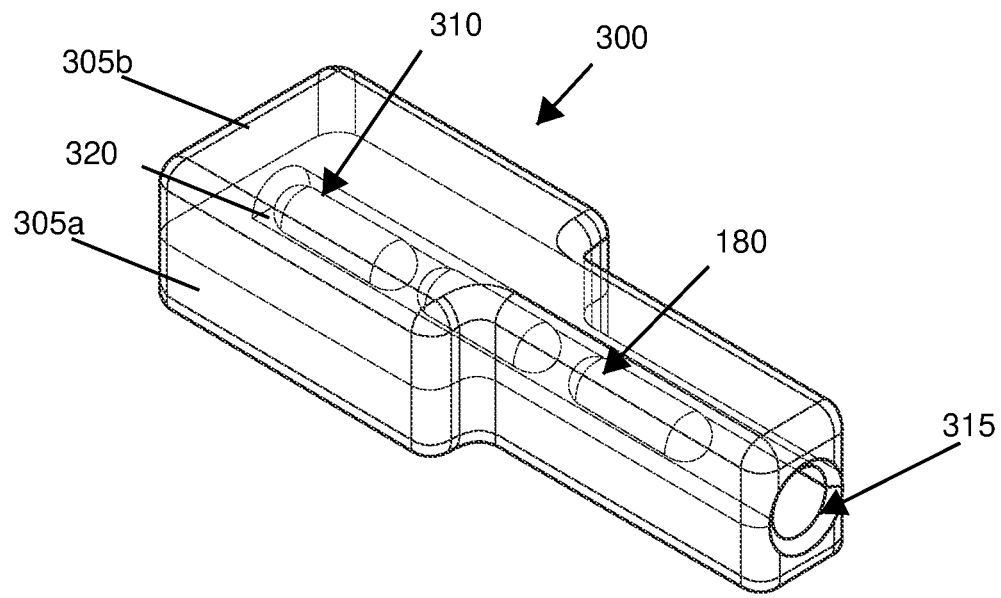
FIG. 5 is a perspective view of an exemplary cartridge that includes capsules for loading into a delivery catheter.

FIG. 5 depicts a perspective view of an exemplary embodiment of a cartridge 300 that is usable to store the payload 180 and to load the payload chamber 175 of the delivery device 100. The cartridge 300 may be particularly useful where the payload 180 is small relative to a human hand and/or fragile, causing it to be difficult to manually load the payload 180 into the payload chamber 175. The cartridge 300 may be formed by two half-shells 305a and 305b coupled together to form a body of the cartridge 300, and that define a hollow interior 310 and an opening 315 providing access to the hollow interior 310. The interior 310 may define a payload channel 320 that extends from the opening 315 and terminating at a closed end within the cartridge 300. The cartridge 300 may be loaded with the payload 180 (e.g., the plurality of individual capsules 185) positioned within the interior channel 320, such that the cartridge 300 is configured to load the distal tip portion 130 in response to the distal tip portion 130 being advanced into the payload channel 320 via the opening 315, as discussed in further detail below. The cartridge 300 may be a single-use device that comes loaded with the payload 180 or may be a reusable device that may be refilled.

At least one of the half-shells 305a and 305b may be at least partially transparent, such that the payload 180 is visible there through. At least one of the half-shells 305a and 305b may include a marking indicative of a quantity of individual capsules included in the payload 180 disposed in the cartridge 300 such as, for example, a coloring, a symbol, text, a structure, a shape of the cartridge 300, or the like.

Figure 6:
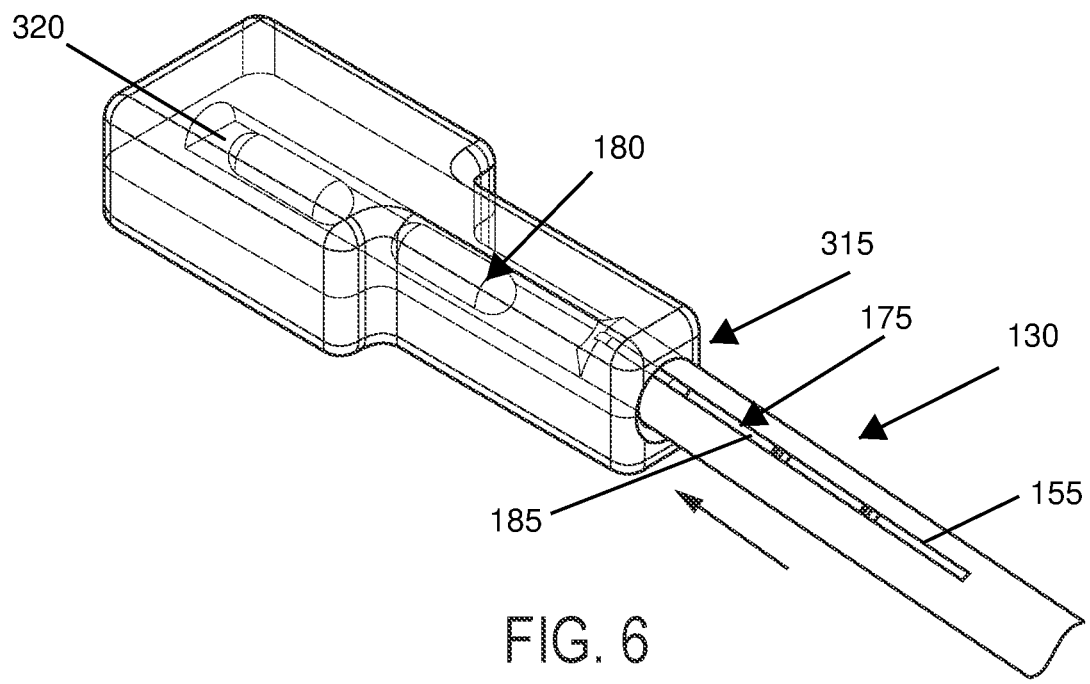
FIG. 6 is a perspective view of the casing of FIG. 5 in use loading a capsule into the distal end portion of the delivery catheter of FIG. 1.

FIG. 6 depicts the distal tip portion 130 of the delivery device 100 being advanced into the payload channel 320 via the opening 315 in order to load the payload 180 into the payload chamber 175 of the distal tip portion 130. As the distal tip portion 130 is advanced, a first of the capsules 185 may be introduced into the payload chamber 175 via the distal opening of working channel 135. As the distal tip portion 130 continues to advance within the payload channel 320, the first of the capsules 185 may be brought into abutment to distal rib 196 defining the most distal of the respective cavities 195.

Further advancement of the distal tip portion 130, e.g., with an increased amount of force, may cause flexure of the shaft 110 via the first slit 155 and the second sit 156, enlarging the constrictive shape of the cavity 195 and enabling the capsule 185 to pass the distal rib 196 defining the distal most cavity 195 and to enter the cavity 195. Additionally or alternatively, the capsule 185 may compress to allow the capsule 185 to pass the distal rib 196 defining the distal most cavity 195 and to enter the cavity 195.

The increase in applied force required to cause the capsule 185 to pass the rib, followed by the release of the force in conjunction with the passage of the capsule into cavity, may result in tactile feedback indicative of the loading of the capsule 185 into the payload chamber 175. This procedure may be repeated in order to load additional capsules into the payload chamber 175, with any previously loaded capsules 185 moving to a respective next-most proximate cavity 195 for each new capsule 185 that is loaded until the payload chamber 175 is full. While the cartridge 300 and the payload chamber 175 in the illustrated example are configured to hold four individual capsules 185, it should be understood that the casing and payload chamber may be configured to hold any number of capsules in other embodiments.

Figure 7F:
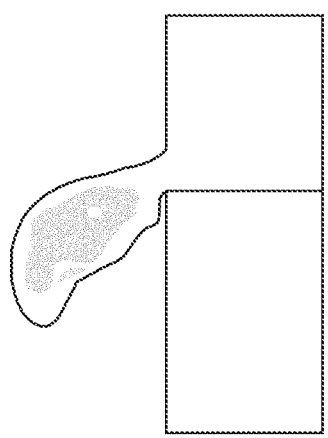
Figure 7G:
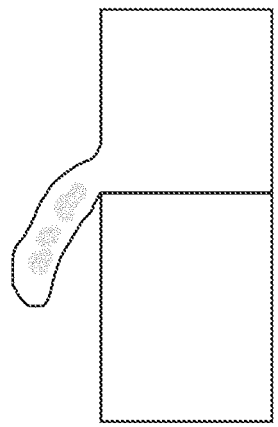
Figure 7H:
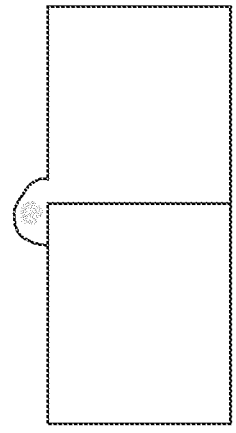

FIGS. 7A-7H depict an exemplary procedure employing the delivery device 100 to deliver the payload 180 to a treatment site 400. In this embodiment, the treatment site 400 includes a cyst 405 that is filled with fluid (e.g., an esophageal cyst). In FIG. 7A, a distal end 410 of a scope device 415 (e.g., an endoscope) may be advanced within a body to the treatment site 400. A guide wire 170 may be introduced into a working channel of the scope device 415, and advanced to the treatment site 400. A proximal end and/or portion of the guide wire 170 (not shown in FIGS. 7A-7H) may be introduced into the guide wire inlet 120 and the guide wire channel 140 of the delivery device 110 (see e.g., FIG. 1), and the shaft 110 of the delivery catheter may be introduced into a proximal end of a working channel of the scope device 415. The guide wire 170 may facilitate the advancement of the shaft 110 along the working channel of the scope device 415 toward the treatment site 400. For example, the guide wire 170 may inhibit formation of a kink in the shaft 110 and/or guide the advancement of the shaft 110 through stringent anatomical curvatures within the body.

In FIG. 7B, the distal tip portion 130 of the delivery device 100 may be advanced out from the working channel of the scope device 415 and into the treatment site 400. In some embodiments, a medical imaging process may be used to observe a location of the distal tip portion 130 within the body. For example, in some embodiments, an ultrasound imaging process may be performed, whereby the echogenic marker 160 (FIG. 2) may be locatable via the ultrasound imaging process to locate the scope device 415 within the treatment site 400 and/or determine whether the distal tip portion 130 has been advanced out from the scope device 415. Any suitable medical imaging process may be used.

In some embodiments, a source of negative pressure (not shown) may be coupled to the fluid connector 125 of the delivery device 100 (FIG. 1) and operated to generate suction within the pair of fluid channels 145 in order to remove at least a portion of the fluid from the treatment site. Removal of at least a portion of the fluid from the treatment site may reduce healing time and/or a frequency or need for future intervention or surveillance of the treatment site 400.

In some embodiments, a source of delivery fluid (not shown) may be coupled to the fluid connector 125 of the delivery device 100 (FIG. 1), and operated to deliver fluid to the treatment site 400. Delivered fluid may include, for example, a bio-active or chemotherapeutic agent, a dye or contrast agent, fluid for irrigating the treatment site, or the like. A bio-active or chemotherapeutic agent delivered to the treatment site 400 may promote healing, inhibit infection, or the like. A dye or contrast agent may facilitate a medical imaging process in locating and/or orienting the distal tip portion 130 of the delivery device 100 within the treatment site 400.

The actuation member 115 (FIG. 1) may be actuated to operate the deployment mechanism 200 (FIG. 4). For example, a user may positively rotate (in a distal direction) the roller knob 215 and cause the pull wire 205 to advance and apply a distal force to the payload 180. As the distal force is applied, the shaft 110 may flex via the first slit 155 and the second slit 156 (FIGS. 2-3), and/or the plurality of capsules 185 may flex or compress in order to enable a most-proximal capsule 185 to pass out from the most-proximal cavity 195 through the distal opening of the working channel 135, and for any distal capsules 185 to advance to a next-most-proximal cavity 195. Upon deployment of the most-proximal capsule 185 through the distal opening of the working channel 135, the applied force may be released, resulting in a tactile feedback to the user at the actuation member 115 via the pull wire 205. The process above may be repeated to deploy additional capsules 185.

In some embodiments, upon depletion of the payload 180 from the housing 100, the delivery device 100 may be retracted from the scope device 415, with the scope device 415 left in place at the treatment site 400. The delivery device 100 may be re-loaded, e.g., via employment of a cartridge 300 that includes a fresh payload 180 (FIG. 6), and may be re-introduced to the scope device 415 and advanced back to the treatment site 400 to deploy the new payload 180.

As shown in FIG. 7C, upon deployment of a desired quantity of capsules 185, the scope device 415 and the delivery device 100 may be retracted out from the body. It may be advantageous for a system to deliver bioabsorbable foam in one or more capsules, e.g., to allow for delivery through a working channel of an endoscope and/or to customize a volume of foam needed for wound treatment. In some embodiments, the delivery device 100 is configured as a single-use device. In other words, after deployment of a desired quantity of the payload 180 and retraction of the delivery device 100, the delivery catheter may be disposed of and/or destroyed.

FIG. 7D depicts the capsules 185 being bio-absorbed and/or dissolved and releasing bio-absorbable foam 450. FIGS. 7E-H depict progression of the bio-absorbable foam absorbing fluid from the treatment site, bio-absorption of the bio-absorbable foam into the body, and reduction of the cyst 405.

Additional aspects of this disclosure may be illustrated in the additional embodiments below. It should be understood that this disclosure is not limited to the specific embodiments described herein, and that features from one or more embodiments may be incorporated into other embodiments.

Figure 8:
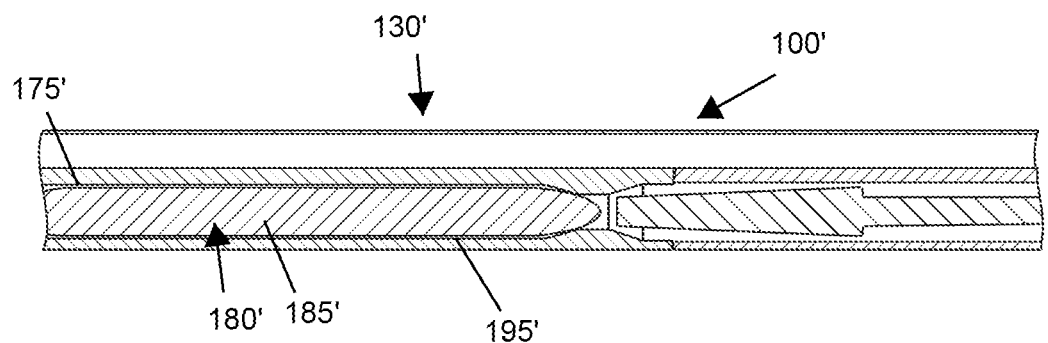
FIG. 8 is a side cross section view of a distal tip portion of a further exemplary embodiment of a delivery catheter.

In various embodiments, any acceptable type of payload may be used. For example, FIG. 8 depicts a distal tip portion 130' of a delivery device 100'. Except where specifically provided, the device 100' may have any of the properties of delivery device 100. A payload chamber 175' of distal tip portion 130' may include only a single cavity 195', and a payload 180' may include a single bio-absorbable extruded tubing structure 185' with bio-absorbable foam disposed therein. The tubing structure 185' may function similarly to a stent, such as a drug-eluting stent. The tubing structure 185' may facilitate directed application of a material (e.g., bio-absorbable foam) contained therein. As compared with capsules 185, tubing structure 185' may contain more material. While delivery device 100' includes only a single cavity 195' for a single tubing structure 185', other embodiments may include any number of cavities and tubing structures. Tubing structure 185' may be delivered as described above for capsules 185. Alternatively, tubing structure 185' may be deployed via alternative delivery devices or methods. For example, tubing structure 185' may be pierced prior to or after delivery to deliver the contents stored therein.

Figure 9:
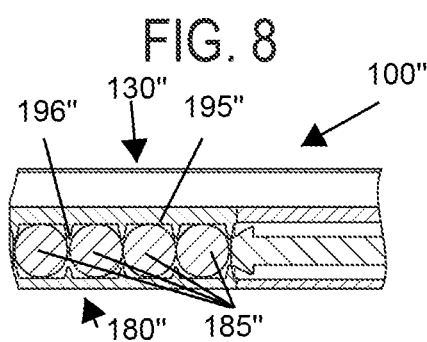
FIG. 9 is a side cross section view of a distal tip portion of a further exemplary embodiment of a delivery catheter.

In another example, FIG. 9 depicts a distal tip portion 130" of a delivery device 100". Except as specifically provided herein, delivery device 100" may have any of the properties of delivery devices 100 or 100'. In this embodiment, a payload 180" may include a plurality of individual spherical beads 185", which may have a smaller longitudinal dimension than capsules 185 or tubing structure 185'. Cavities 195" may be correspondingly longitudinally shorter, with protrusions 196" being longitudinally closer to one another. Device 100" may function as device 100 does, described above.

A reduced longitudinal extent of the beads 185" relative to other shapes for the payload 180" (e.g., capsules 185 or tubing structure 185') may result in a decreased length of the distal tip portion 130", which may be relatively rigid. A reduced length of the distal tip portion 130" may facilitate advancement of the delivery device 100" through tight anatomical curvatures, and may reduce an extent to which the delivery device 100" is required to be advanced out from the working channel of a scope device to facilitate deployment of the payload 180". In other embodiments, the payload 180" may have any other acceptable shape such as, for example, an ovoid shape, a disk shape, a cube shape, a cylinder shape, etc.

Figure 10:
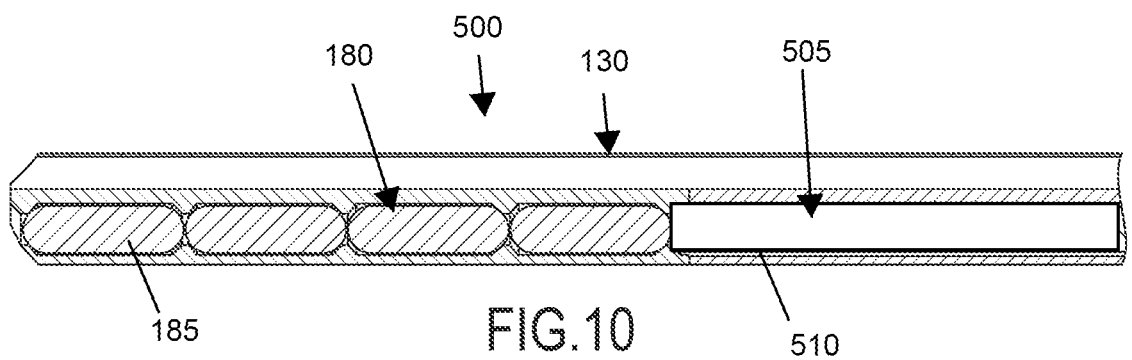
FIG. 10 is a side cross section view of a distal tip portion of a further exemplary embodiment of a delivery catheter.

FIG. 10 depicts another example delivery device 500, which may have any of the properties of delivery devices 100, 100', 100". The distal end 130 of device 500 may be the same as the distal end 130 of delivery device 100. Alternatively, distal ends 130', 130" may be utilized. A deployment mechanism 505 (which may have some features of deployment mechanism 200) may include a pressure channel 510. A handle portion of delivery device 500 may be the same as handle portion 105 of delivery device 100 and may include a trigger mechanism. Any acceptable trigger mechanism may be used. In some embodiments, for example, the roller knob 215 may operate as the trigger mechanism. In some embodiments, the handle portion may include a further actuation member (e.g., a trigger, a lever, a knob, a slider, or other structure) that operates as the trigger mechanism. In an example, the trigger mechanism may be configured to selectively couple the pressure channel 500 with a positive pressure source. For example, a positive pressure source may be connectable via a feature such as fluid connector 125 of device 100. A presence of positive pressure in the pressure channel 500 may result in a distal force on the payload 180 toward the distal end of the distal end portion 130. The positive pressure may be configured such that the distal force is sufficient to actuate the payload 180, e.g., actuate each capsule 185 toward the distal end of distal end portion 130 and deploy at least a most-distal capsule 185.

In some embodiments, the trigger mechanism may be configured to couple the pressure channel 500 to the positive pressure for a discrete period of time for each actuation of the trigger mechanism, or may be configured to convey a discrete portion of pressure medium, or the like. For example, in some embodiments, the trigger mechanism may be configured such that each actuation of the trigger mechanism results in deployment of a single capsule 185 of the payload 180.

Figure 11:
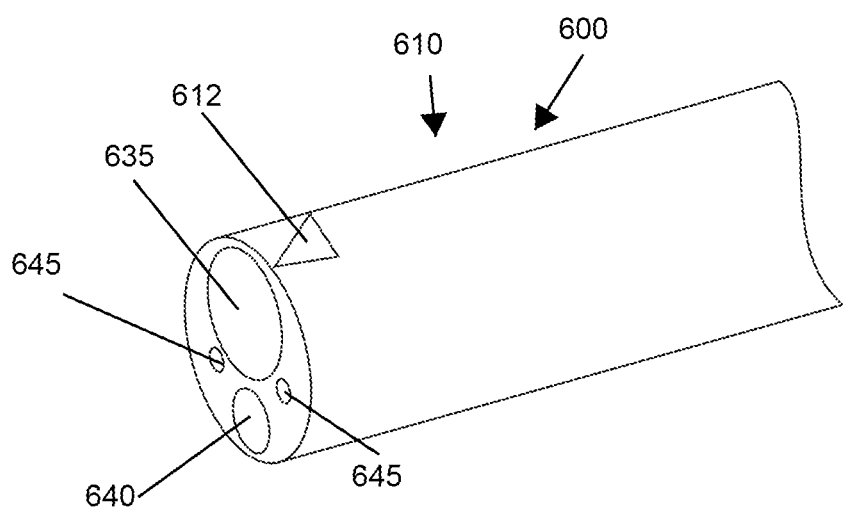
FIG. 11 is a perspective view of a distal end of a tubular portion of a further exemplary embodiment of a delivery catheter.

FIG. 11 is a perspective view of the distal end of a shaft 610 of an exemplary delivery device 600 in which a distal tip portion 630 is a separate piece from the shaft 610. Shaft 610 and distal tip portion 630 may otherwise have any of the properties of shaft 110 and distal tip portion 130. Shaft 610 may define four channels—a working channel 635, a guide wire channel 640, and two fluid channels 645, which may have any of the properties of working channel 135, guide wire channel 140, and fluid channels 145, respectively.

The shaft 610 may further include a first alignment indicator 612 indicative of an orientation of the channels 635, 640, 645 within the shaft 610. For example, alignment indicator may be an arrow or a triangle pointing toward a distal end of shaft 610. As shown in FIG. 10, indicator 612 may be aligned with working channel 635.

Figure 12:
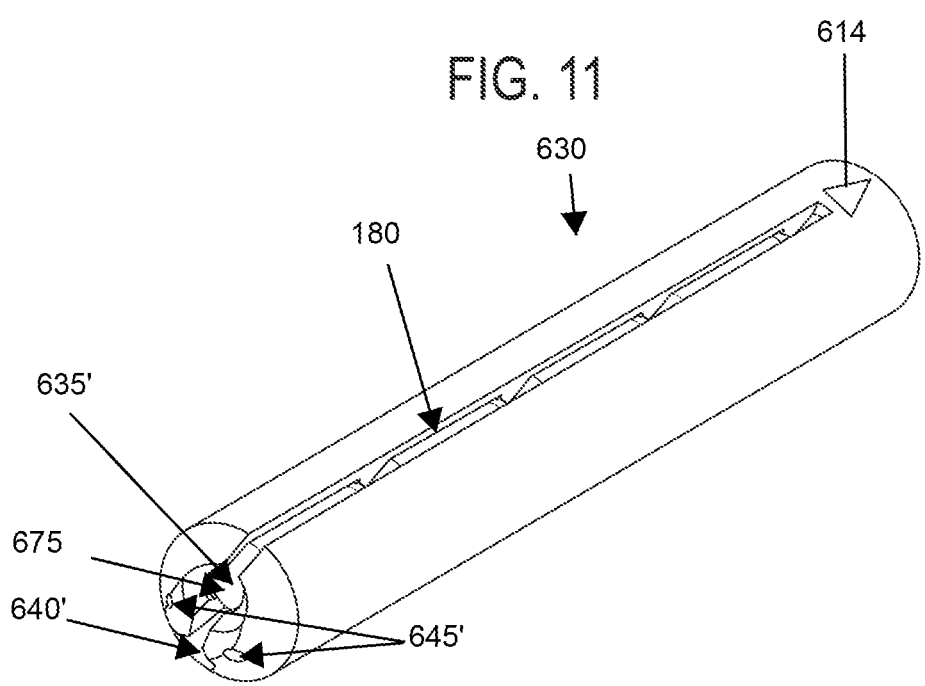
FIG. 12 is perspective view of a further exemplary embodiment of a distal tip portion for a delivery catheter.

FIG. 12 is a perspective view of an exemplary embodiment of the distal tip portion 630 that is a separate piece from the shaft 610 of FIG. 11. The distal tip portion 630 may define channels lumens that may be configured to be put in communication with the channels of shaft 610. For example, the distal tip portion 630 may define a distal tip working channel 635', a distal tip guide wire channel 640', and two distal tip fluid channels 645'. The channels of the distal tip portion 630 may have any of the qualities of the channels of the distal tip portion 130.

The distal tip portion 630 may include a second alignment indicator 614 that is indicative of an orientation of the distal tip portion 630, and is configured to facilitate coupling of a proximal end of the distal tip portion 630 to the distal end of the shaft 610 so that channels of the distal tip 630 are aligned with the channels of shaft 610. For example, the second alignment indicator 614 may include an arrow or a triangle pointing proximally. The second alignment indictor 614 may be aligned with distal tip working channel 635'.

The distal tip portion 630 may be loaded (e.g., preloaded) with a payload 180 positioned in a payload chamber 675, having any of the properties of the payload chamber 175. Therefore, the delivery device 600 may be loaded via the coupling of the distal tip portion 630 to the shaft 610. When the distal tip portion 630 is depleted of payload 180, distal tip portion 630 may be de-coupled from the shaft 610 and replaced with a fresh distal tip portion 630.

Any acceptable type of coupling between the proximal end of the distal tip portion 630 and the distal end of the shaft 610 may be used such as, for example, a screw connection, a key- and slot connection, a pin connection, an interference fit, or the like. Any acceptable alignment indicator(s) may be used for the first alignment indicator 612 and the second alignment member 614 such as, for example, a visual indication of an orientation of the respective portions, a structure that inhibits a misalignment (e.g., a protrusion), or the like.

Figure 13:
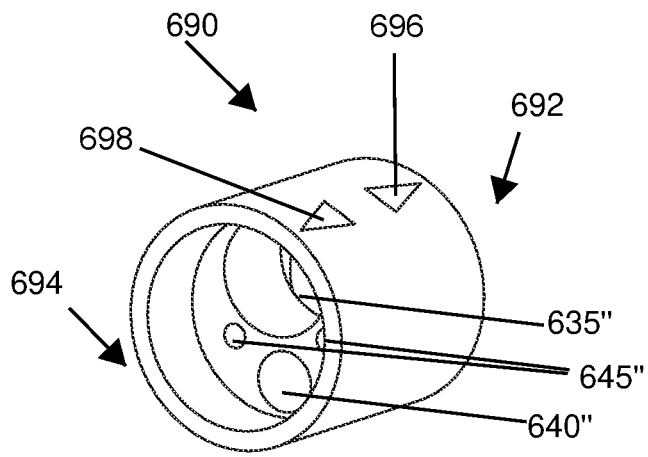
FIG. 13 is a perspective view of an exemplary embodiment of a coupling member.

FIG. 13 is a perspective view of an exemplary embodiment of a coupling member 690 configured to facilitate the coupling between the distal tip portion 630 and the distal end of the shaft 610. The coupling member 690 may include a first end 692 configured to couple directly with the distal end of the shaft 610, and a second end 694 configured to couple directly with the proximal end of the distal tip portion 630 in order to couple the distal tip portion 630 to the shaft 610. The first end 692 and the second end 620 may be sized to form an interference fit with the distal end of the tubular member 610 and the proximal end of the distal tip portion 630, respectively. In other embodiments, any acceptable coupling technique may be used. The coupling member 690 may include a sealing element (not shown), e.g., an O-ring, a flange, or the like configured to seal the coupling between the distal tip portion 630 and the shaft 610.

Coupling member 690 may define four channels, corresponding to the channels of the shaft 610 and the distal tip portion 630. For example, the coupling member 690 may define a coupling member working channel 635", a coupling member guide wire channel 640", and two coupling member fluid channels 645". The channels of coupling member 690 may be configured to be in fluid connection with corresponding channels of shaft 610 and distal tip portion 630.

The coupling member 690 may include a third alignment member 696 configured to align the coupling member 690 with the shaft 610. For example, the third alignment member 696 may include a proximal-facing arrow or triangle. The third alignment member 696 may be used in conjunction with the first alignment member 612 of the shaft 610 to align the channels of the alignment member 696 with the channels of the shaft 610. For example, tips of the triangles/arrows of the first alignment member 612 and the third alignment member 696 may be aligned with one another when coupling shaft 610 to coupling member 690. Coupling member may also include a fourth alignment member 698 that is usable in conjunction with the second alignment member 614 to align the distal tip portion 630 with the coupling member 690, and thus with the shaft 610. For example, tips of the triangles/arrows of the second alignment member 614 and the fourth alignment member 698 may be aligned with one another when coupling the distal tip portion 630 to the coupling member 690. Alternatively, the third and fourth alignment members 696, 698 may be combined into one alignment member. In some embodiments, the first and second alignment members include a longitudinally or radially extending rib or groove, and the third and fourth alignment members include a corresponding groove or rib, respectively.

Figure 14:
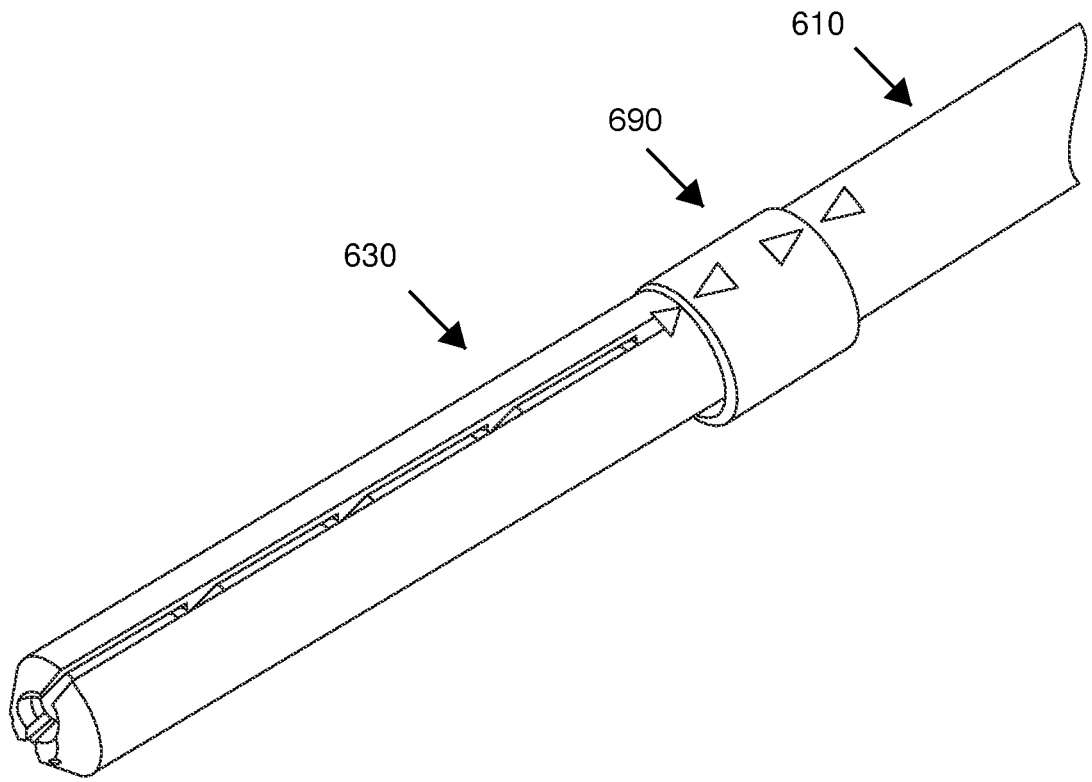
FIG. 14 is a perspective view of an assembly of the distal end of FIG. 11, the distal tip portion of FIG. 12, and the coupling member of FIG. 13.

FIG. 14 is a perspective view of an assembly of the shaft 610, coupling member 690, and the distal tip portion 630. The alignment members have been aligned with one another in order to couple the corresponding channels of the shaft 610 and the distal tip portion 630 together. In an alternative, coupling member 690 may be omitted, and shaft 610 may be coupled directly to distal tip portion 630.

Figure 15:
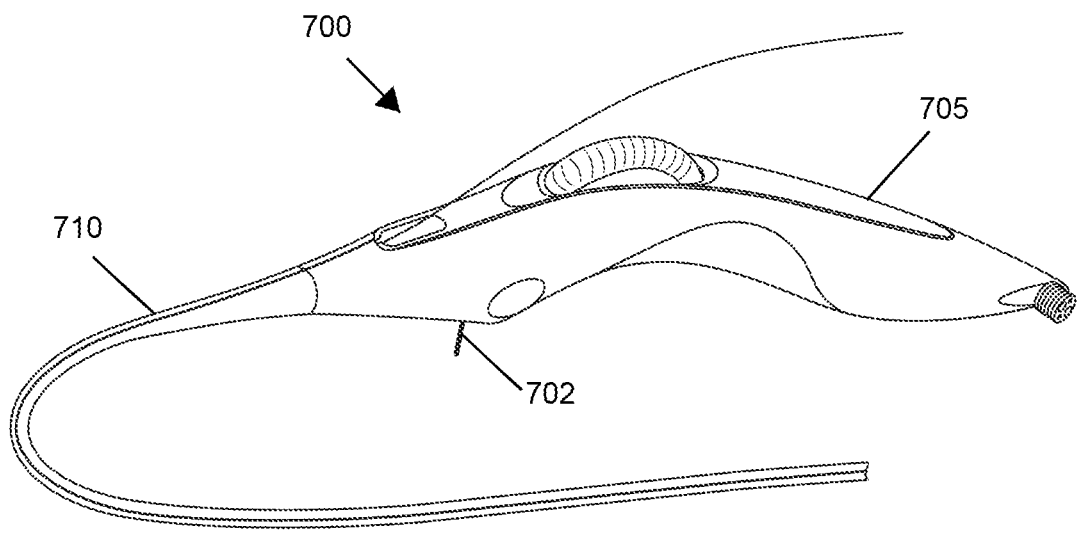
FIG. 15 is a perspective view of a further exemplary embodiment of a delivery catheter.

FIG. 15 depicts a perspective view of a delivery device 700. Delivery device 700 may have any of the properties of any of the delivery devices herein, except where specifically described. Handle portion 705 may further include a cautery connector 702 that is configured to couple with a cautery device (not shown).

Figure 16:
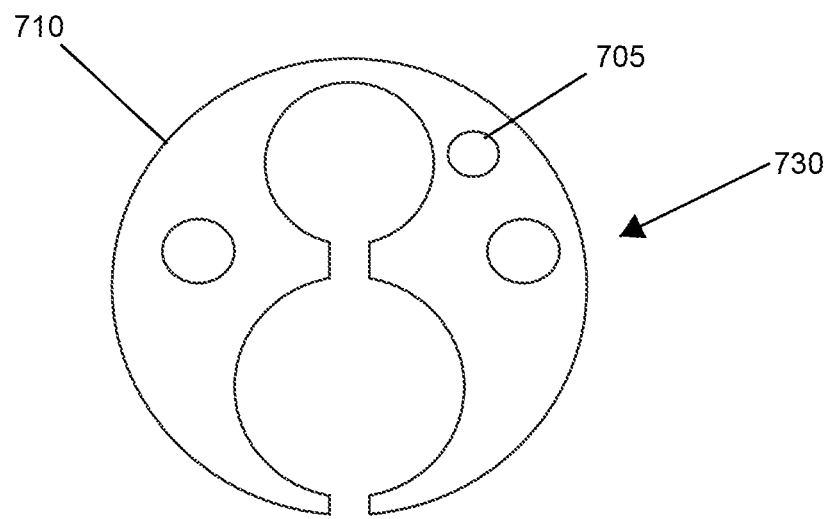
FIG. 16 is an end view of a tubular portion of the delivery catheter of FIG. 15.

FIG. 16 depicts an end view of distal end portion 730 of a shaft 710 of the delivery device 700 of FIG. 15. Shaft 710 may have any of the features of shaft 110 or the other shafts described herein, except where specified. As shown in FIG. 16, the shaft 710 may define a cautery lumen 705. The cautery lumen 705 may extend along an length of the shaft 710, and may operatively connected to the cautery connector 702, such that the cautery connector 702 is configured to operatively couple the cautery lumen 705 to the cautery device. The cautery lumen 705 may, for example, be configured to pass a cautery wire of the cautery device therethrough and/or may operate as a cautery wire of the cautery device.

Figure 17:
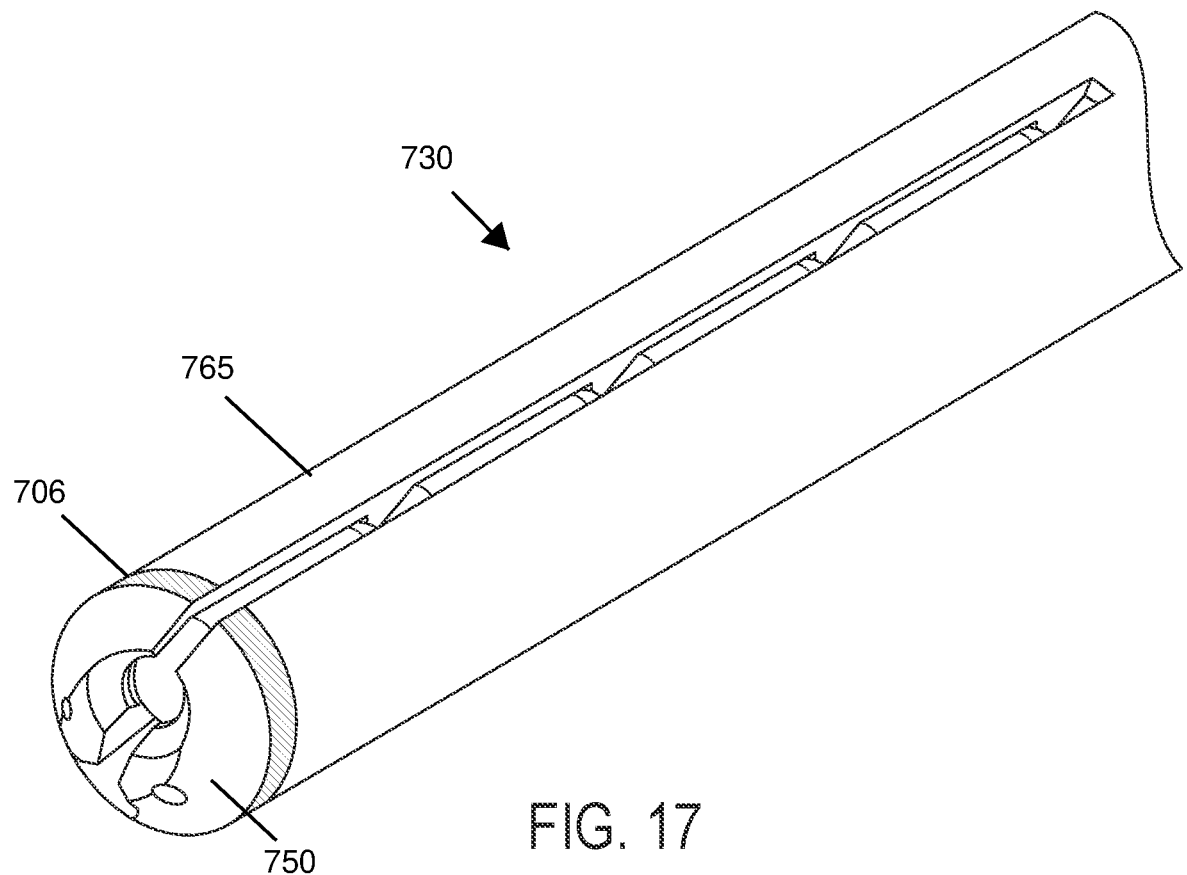
FIG. 17 is a perspective view of a distal tip portion of the delivery catheter of FIG. 15.

FIG. 17 depicts a perspective view of the distal tip portion 730 of the delivery device 700 of FIG. 15. Distal tip portion may have any of the properties of any of the distal tip portions described herein, including distal tip portion 130. As shown in FIG. 17, the distal tip portion 730 further includes a cautery member 706, e.g., a cautery ring, positioned about a circumferential outer surface 765 of the distal tip portion 730. Cautery member 706 may have alternative forms and may be disposed on a distal face 750 of distal tip member 730 and may have any suitable shape. In various embodiments, the cautery member 706 may be operated (e.g., via the cautery device coupled to the cautery connector 700) to cauterize at least a portion of the treatment site 400 and/or enable access for the delivery device 700 to internal sites within the body such as an organ like the pancreas, or the like by forming openings through which the delivery device 700 may pass.

Figure 18:
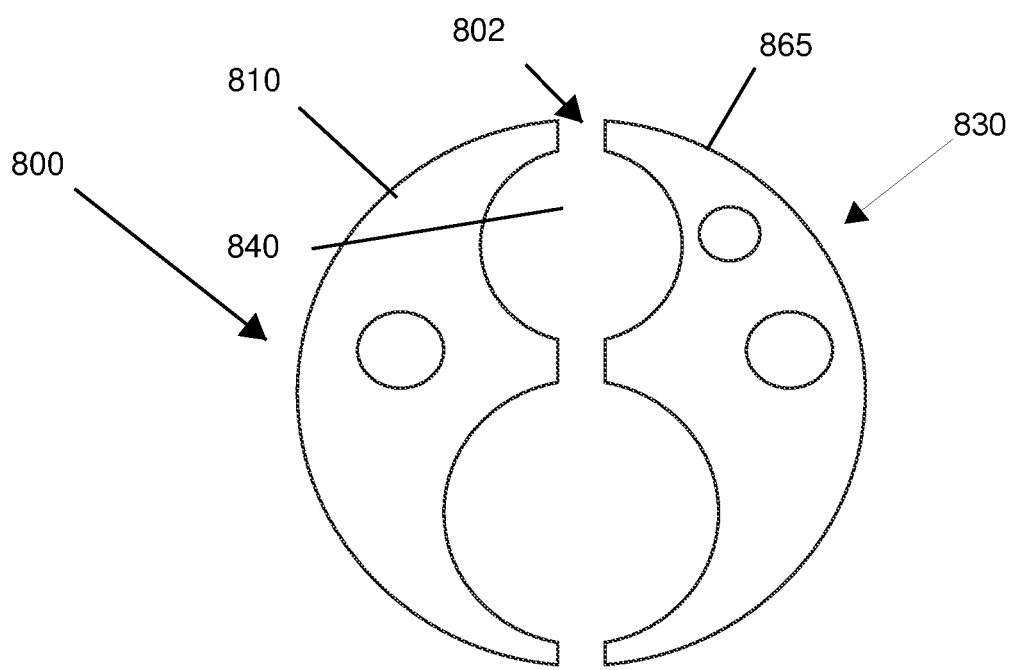
FIG. 18 is an end view of a tubular portion of a further exemplary embodiment of a delivery catheter.

FIG. 18 depicts an end view of a shaft 810 of a delivery device 100, which may have any of the properties of the other delivery devices described herein, except as specified. Shaft 810 may further define a third slit 802 that extends through a wall of distal tip portion 830, connecting an outer surface 865 of the shaft 810 to a guide wire channel 840. The third slit 802 may extend along at least a portion of a length of the shaft 810, between a distal tip portion 830 and a guide wire inlet, such as guide wire inlet 120. The third slit 802 may be a substantially similar or same length as the first slit 155. The third slit 802 may extend along the length of the shaft 810. The third slit 802 may be sized and configured to enable the shaft 810 to flex (and the third slit 802 to widen) in order to pass the guide wire 170 through the third slit 802 and into the guide wire channel 840.

The delivery device 800 may be removed from the guide wire via slit 802 without retracting the delivery device 100 over a full extent of the guide wire 170. Rather than inserting an end of the guide wire 170 into the guide wire channel 840, and advancing the delivery device 800 along the guide wire 170 so that the guide wire 170 advances out from the guide wire inlet, as discussed above, a portion of the guide wire 170 may be inserted into the guide wire channel 140 and the guide wire inlet 120 via the third slit 802, such that the guide wire 170 protrudes out from the guide wire inlet without a need to advance the delivery device 100 along the guide wire 170. Third slit 802 may facilitate simple and rapid insertion, removal, and or exchange of the delivery device 800.

Figure 19A:
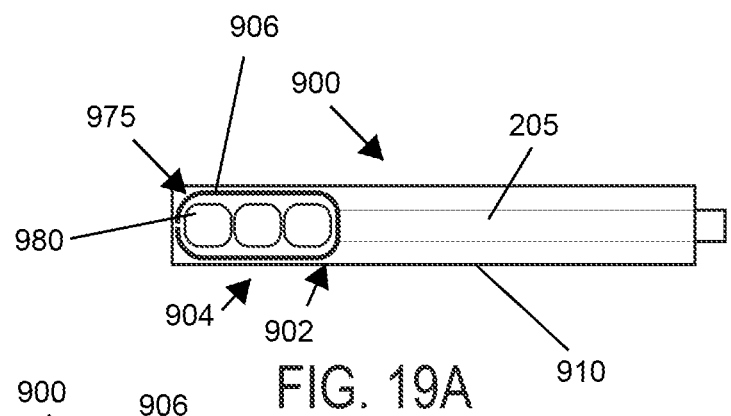
FIGS. 19A-19C are illustrations that depict a distal tip portion of a further exemplary embodiment of a delivery catheter in use to deploy material.
Figure 19B:
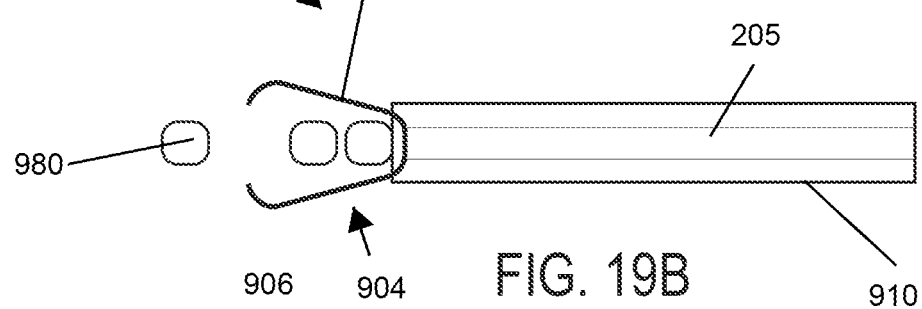
Figure 19C:
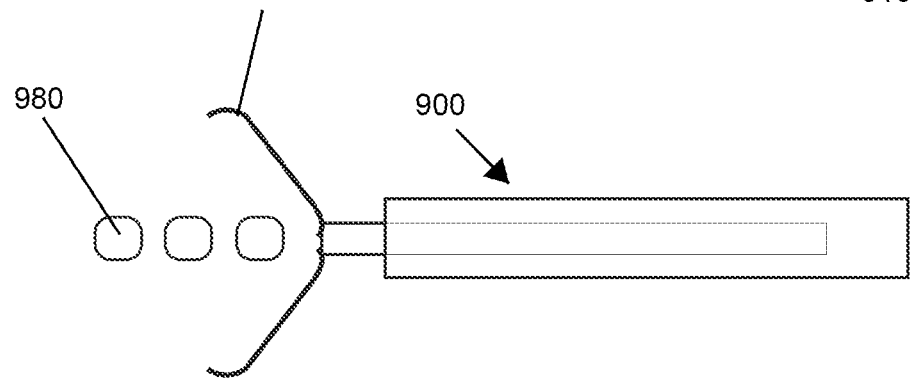

FIGS. 19A-C depict operation of a further exemplary embodiment of a delivery mechanism 902 of a delivery device 900. Delivery device 900 may have any of the features of the other delivery devices disclosed herein. Delivery device 900 may include the handle portion 105 (not shown).

A delivery mechanism 902 may include a grasper mechanism 904 that is operatively connected to the actuation member 115 via the pull wire 205. The grasper mechanism 904 may include a plurality (e.g., a pair) of arms 906. Arms 906 may have distal ends that curve radially inward, toward a central longitudinal axis of a shaft 910 of the delivery device 900.

The grasper mechanism 904, in a retracted position of the pull wire 205, may extend distally into a payload chamber 975. In a closed position, as depicted in FIG. 19A, the distal ends of the arms 906 may be sufficiently close together such that the grasper mechanism 904 holds a payload 980 (which may have properties of any of the payloads described herein) in place within the payload chamber 975, such that payload 980 may not pass distally of arms 906.

The arms 906 of the grasper mechanism 904 may be biased, e.g., via an internal resilience, a spring member, a shape memory material, or the like, toward an open position such that, as the pull wire 205 is advanced and a distal end of the grasper mechanism 904 is advanced out from a distal end of the shaft 910, the grasper mechanism 906 actuates toward an open position (see FIG. 19B). The arms 906 of the grasper mechanism 904 may open so that the distal ends of the arms are spread apart from one another, allowing the payload 180 to be deployed (see FIG. 19C). The grasper mechanism 904 may be further shaped and configured such that as the pull wire 205 is retracted, the grasper mechanism 904 is brought into abutment with the distal end of the shaft 910, and is moved toward the closed position.

Figure 20:
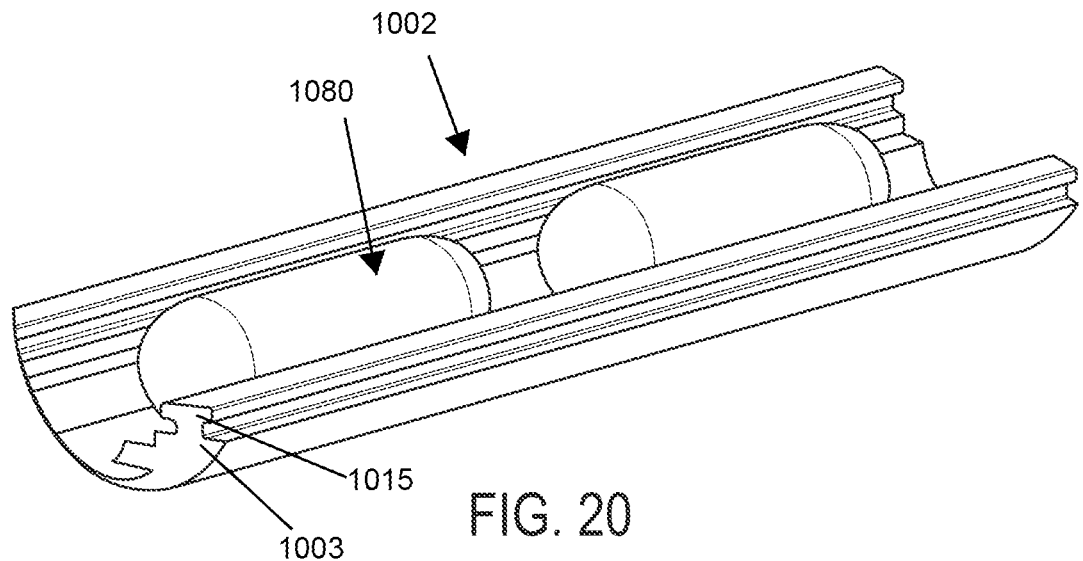
FIG. 20 is a perspective view of a further exemplary embodiment of a distal tip portion for a delivery catheter.

FIGS. 20-23 depict another example of a medical device 1000. FIG. 20 shows a cartridge piece 1002 to be coupled with a shaft 1010 of a delivery device 1000. The cartridge piece 1002 may be pre-loaded with a payload 1080, which may have any of the properties of the payloads disclosed herein. Cartridge piece 1002 may be configured to be loaded onto a distal end of the shaft 1010, as discussed in further detail below. The cartridge piece 1002 may be formed of wall 1003 that has a generally arcuate or semi-circular shape.

Figure 21:
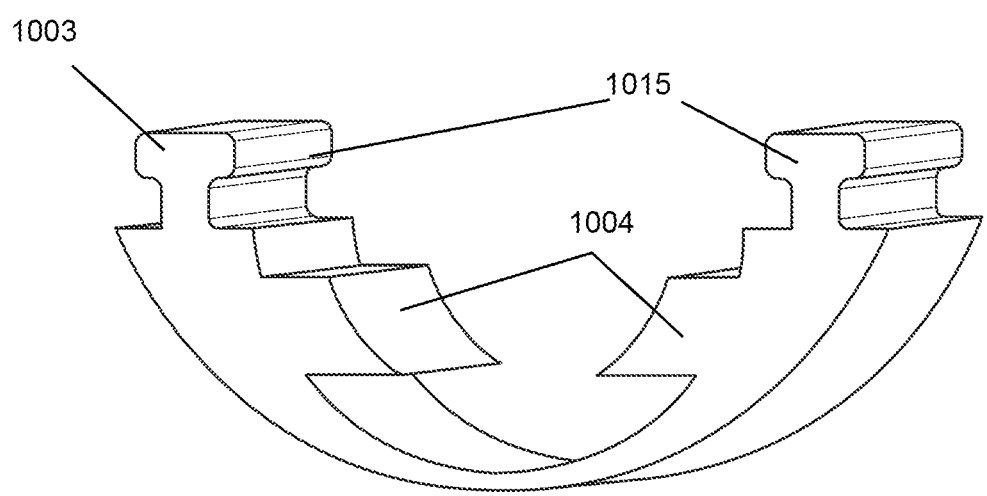
FIG. 21 is a perspective view of a cross-section of the distal tip portion of FIG. 20.

FIG. 21 is a perspective view of a cross sectional slice of the cartridge piece 1002 of FIG. 20. As shown in FIG. 21, wall 1003 may define a first protruding structure 1004 configured to support the payload 1080 in alignment with the working channel 1035 of the shaft 1010, and/or to prevent the payload 1080 from sliding distally out of the delivery device 1000. Wall 1003 may also define two slide structures 1015 (e.g., protrusions), configured to mate with portions (e.g., recesses) of the shaft 1010, as described below. Each slide structure 1015 may have a T-like shape, as shown in FIG. 21. However, any suitable shape may be used. The payload 1080 may be received by inner surfaces of the wall 1003.

Figure 22:
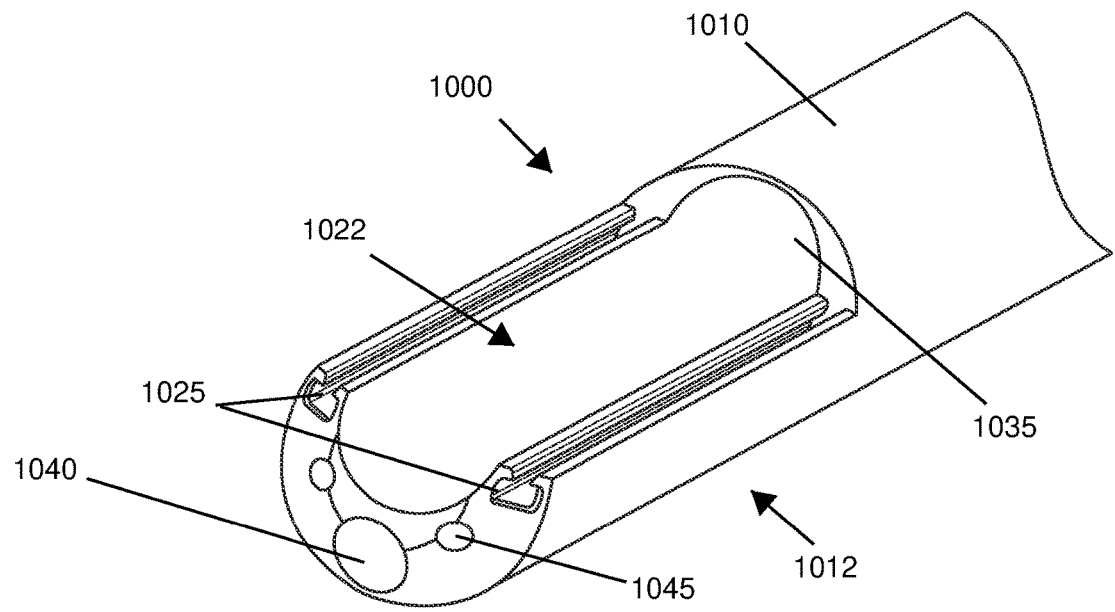
FIG. 22 is a perspective view of a distal end of a tubular portion of a further exemplary embodiment of a delivery catheter.

FIG. 22 is a perspective view of the distal end 1012 of the shaft 1010. A portion of the shaft 1010 defining a guide wire lumen 1040 and fluid lumens 1045 may continue through distal end 1012. A wall of the shaft defining a portion of the working channel 1035 may terminate prior to the distal end 1012, such that the working channel 1035 terminates prior to the distal end 1012. A cavity 1022 may be formed by portions of walls that continue distally from the working channel 1035. The cavity 1022 may receive the payload 1080 after the cartridge piece 1002 is coupled to the distal end 1012.

The walls of distal end 1012 may have a complementary shape to the cartridge piece 1002, such that the cartridge piece 1002 and the distal end 1012 may form a tubular shape when assembled together, continuous with a remainder of shaft 1010. For example, the walls of the distal end 1012 may have an arc shape or a semi-circular shape. The walls of distal end 1012 may include rail structures 1025 (e.g., recesses) that are configured to slideably receive the slide structures 1015 of the cartridge piece 1002 in order to couple the cartridge piece 1002 to the distal end 1012 of the shaft 1010.

Figure 23:
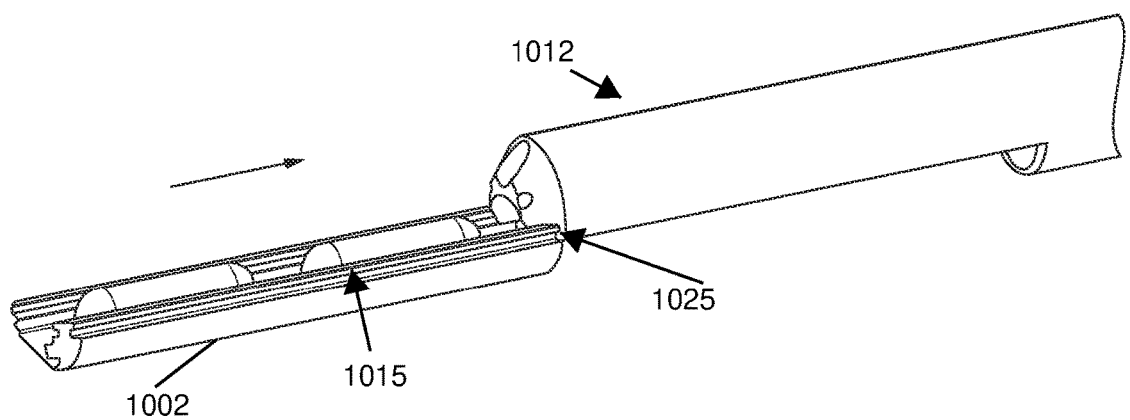
FIG. 23 is a perspective view of the distal tip portion of FIG. 20 being coupled to the distal end of the tubular portion of FIG. 22.
Figure 24:
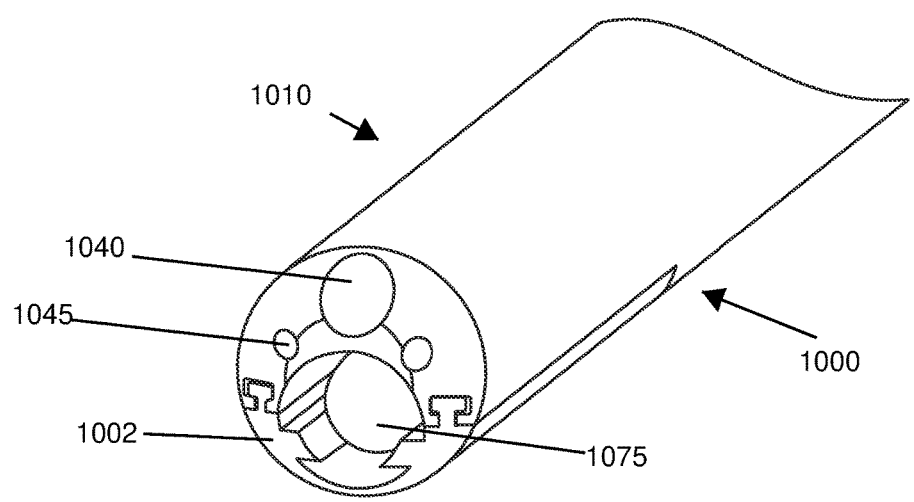
FIG. 24 is a perspective view of an assembly of the distal tip portion of FIG. 20 and the distal end of the tubular portion of FIG. 22.
Figure 25:
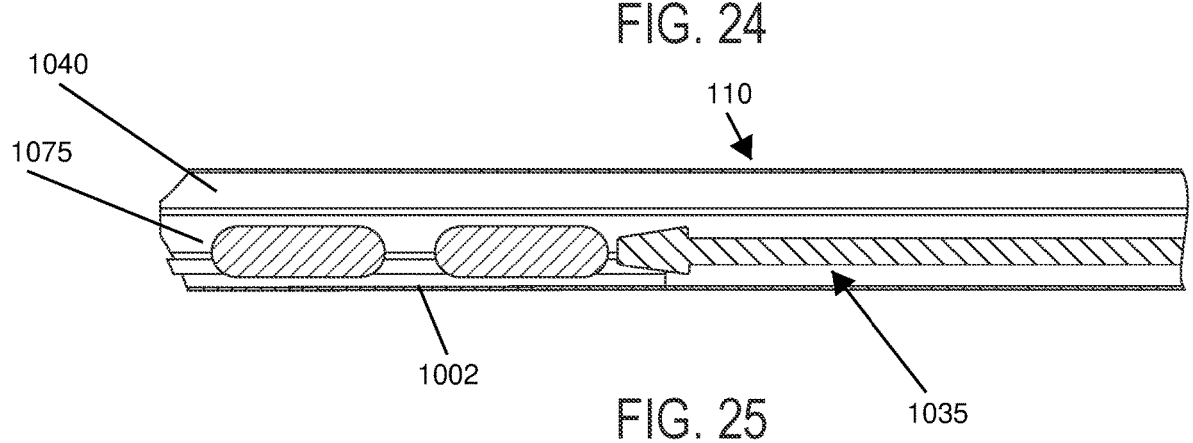
FIG. 25 is a side cross section view of the assembly of FIG. 24.

FIG. 23 depicts a perspective view of the slide structure 1015 of the cartridge 1000 being introduced into the rail structure 1025 of the distal end 1012. FIGS. 24 and 25 depict a perspective view and a side cross section view, respectively, of an assembly of the cartridge piece 1002 with the shaft 1010. As shown in FIGS. 24 and 25 when the cartridge piece 1002 is fitted on the shaft 1010, a payload chamber 1075 is formed by walls of the cartridge piece 1002 and the shaft 1010. The payload chamber 1075 may be in communication with the working channel 1035.

Figure 26:
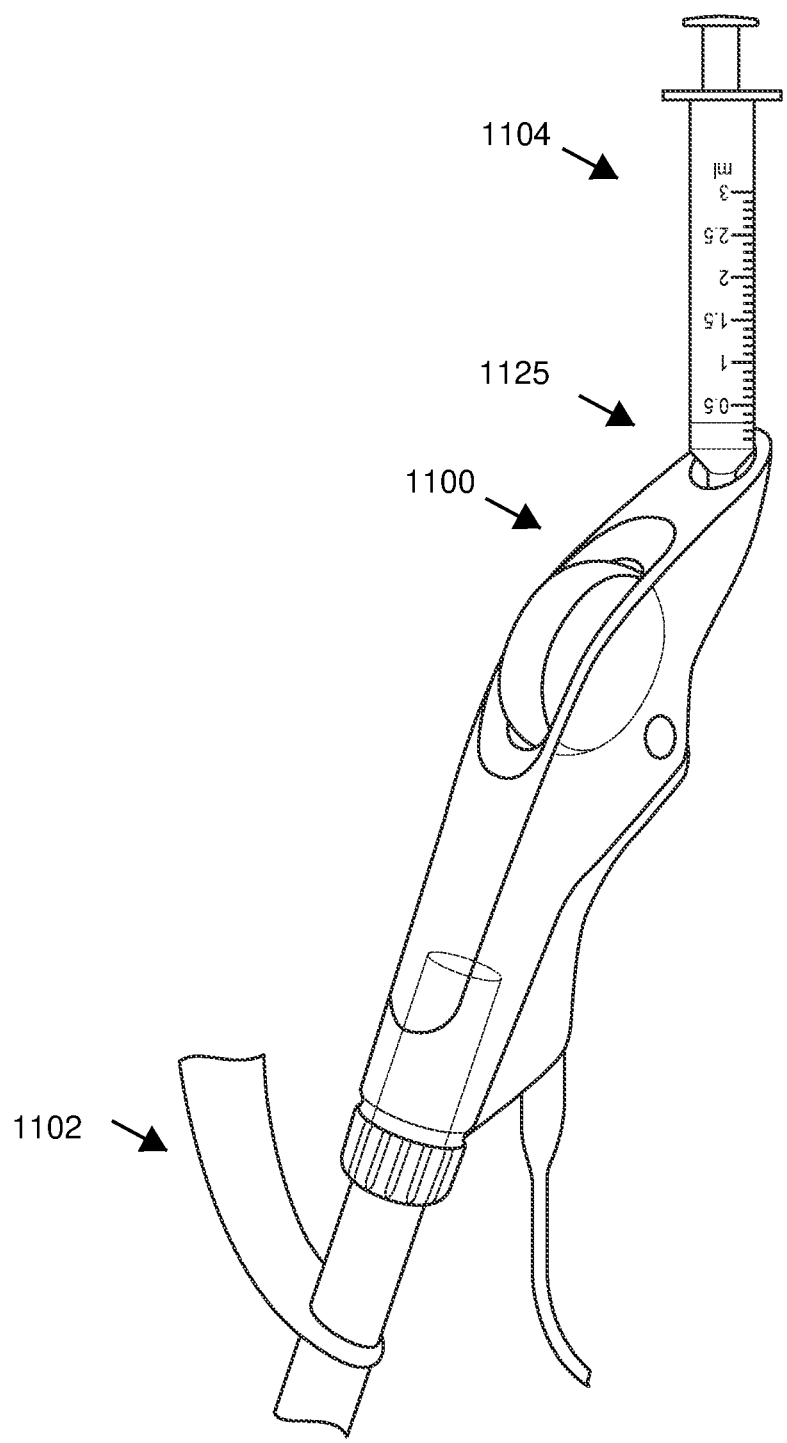
FIG. 26 is a perspective view of a further exemplary embodiment of a delivery catheter.

FIG. 26 depicts a perspective view of another exemplary delivery device 1100. The delivery device 1100 may further include a connection member 1102 configured to removably couple the delivery device 1100 to a scope device (e.g., an endoscope). The connection member 1102 may include a clamp, clip, or the like configured to removably attach the delivery device 1100 to the scope device. The connection member 1102 may include a strap configured to wrap around a handle of the scope device. Any suitable type of connection member 1102 may be used. When coupled to the scope device, the delivery device 100 may be operated in a partially hands-free manner (e.g., one-handed), or a completely hands-free manner. Connection member 1102 may include a locking ring, strap, a clamp, a lock, an arm, a mating surface, or any other suitable component. Delivery device 1100 also depicts a syringe 1104 connected to a fluid connector 1125, which may have any of the properties of fluid connector 125. The syringe may be used to, e.g., provide suction or negative pressure via a fluid lumen of the delivery device 1100.

Any of the shafts disclosed herein may include at least one manipulation lumen. The manipulation lumen(s) may receive articulation wires or other structures which may be used to steer and/or deflect a distal end of the shaft. For example, in a procedure to deliver bio-absorbable foam to the treatment site an echogenic marking may be used to determine an orientation of a distal tip of the shaft (e.g., after the distal tip has been advanced from a scope, as shown in FIG. 7B). In the case that the distal tip of the shaft is not optimally oriented relative to the treatment site, the at least one manipulation lumen may be utilized (e.g., via an articulation wire in the manipulation lumen) in order to reorient a distal to of the shaft, which may be further observed via the echogenic marking 160.

Each of the aforementioned systems, devices, assemblies, and methods may be used to treat a perforation, wound, or cyst by deploying a payload (e.g., bio-absorbable foam) for absorbing fluids and/or delivering therapeutic substances thereto. By providing a medical device with an intuitive handle interface capable of controlling a deployment of the payload with a single hand, a user may utilize another hand to control other devices and/or tools during a procedure for treating the target site. In this instance, a user may reduce overall procedure time, increase efficiency of procedures, and/or avoid unnecessary harm to a subject's body caused by limited control of the other tools/devices.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
   a handle portion including a fluid connection configured to connect with at least one of a source of negative pressure or a source of delivery fluid;
   a shaft portion extending distally from the handle portion, and including:
      a working channel;
      a pair of fluid channels configured to selectively pass fluid and negative pressure there-through, wherein the fluid connection is in fluid communication with the pair of fluid channels;
      a guide channel configured to pass a guide wire there-through; and
      a distal tip portion including:
         a payload chamber configured to receive a payload, and operatively connected to the working channel;
         a pair of distal fluid openings operatively connected to the pair of fluid channels; and
         a distal guide wire opening operatively connected to the guide channel;
   a deployment mechanism positioned in the working channel, and operable to deploy the payload out from the distal tip portion; and
   an actuation member, positioned on the handle portion, actuatable to operate the deployment mechanism.

2. The medical device of claim 1, wherein the distal tip portion defines a slit extending through a wall of the distal tip portion, wherein the slit is configured to enable the distal tip portion to flex in order to receive and deploy the payload.

3. The medical device of claim 1, wherein:
   the shaft portion further includes:
      a slit extending through a side-wall of the shaft portion to the guide channel and along a length of at least a portion of the shaft portion, the slit being configured to pass at least a portion of a length of the guide wire there-through.

4. The medical device of claim 1, wherein an inner surface of the payload chamber defines a plurality of cavities configured to receive the payload.

5. The medical device of claim 1, wherein the distal tip portion defines a slit between the working channel and an outer surface of the distal tip portion, and wherein the actuation of the actuation member causes the slit to expand.

6. The medical device of claim 1, wherein the distal tip portion is a separate piece from the shaft portion, and wherein the distal tip portion is configured to couple with a distal end of the shaft portion.

7. The medical device of claim 6, wherein the distal tip portion is preloaded with the payload prior to coupling with the distal end of the shaft portion.

8. The medical device of claim 7, further comprising:
   a coupling member including:
      a first end configured to couple directly with the distal end of the shaft portion;
      a second end opposite the first end configured to couple directly with a proximal end of the distal tip portion in order to couple the distal tip portion to the shaft portion; and
      at least one alignment element configured to align the shaft portion with the distal tip portion.

9. The medical device of claim 1, wherein the shaft portion further includes a cautery lumen;
   the handle portion includes a cautery connector configured to operatively couple the cautery lumen to a cautery device; and
   the distal tip portion further includes a cautery element positioned on an outer surface of the distal tip portion.

10. The medical device of claim 1, wherein:
    the deployment mechanism includes:
       a pull wire; and
       a plunger positioned at a distal tip of the pull wire; and
    the actuation member includes a roller knob operatively engaged with a proximal end of the pull wire.

11. The medical device of claim 1, wherein the handle portion includes a connection member configured to removably couple the medical device to a scope device.

12. The medical device of claim 1, wherein the distal tip portion further includes at least one echogenic marking positioned on an outer surface of the distal tip portion.

13. A medical device, comprising:
    a delivery catheter, including:
       a handle portion including a fluid connection configured to connect with at least one of a source of negative pressure or a source of delivery fluid;
       a shaft portion extending distally from the handle portion, and having:
          a working channel;
          a pair of fluid channels configured to selectively pass fluid and negative pressure there-through, wherein the fluid connection is in fluid communication with the pair of fluid channels;
          a guide channel configured to pass a guide wire there-through; and
          a distal tip portion including:
             a payload chamber configured to receive a payload, and operatively connected to the working channel;
             a pair of distal fluid openings operatively connected to the pair of fluid channels; and
             a distal guide wire opening operatively connected to the guide channel;
       a deployment mechanism positioned in the working channel, and operable to deploy the payload out from the distal tip portion; and
       an actuation member positioned on the handle portion, and that is actuatable to operate the deployment mechanism; and
    a cartridge, including:
       an opening formed on a surface of the cartridge, the opening configured to provide access into an interior of the cartridge and to receive the distal tip portion of the delivery catheter; and a bio-absorbable foam payload positioned in the interior and arranged such that the cartridge is configured to load the distal tip portion with the payload in response to the distal tip portion being advanced into the cartridge via the opening.

14. The medical device of claim 13, wherein the cartridge includes two half-shells coupled together.

15. The medical device of claim 14, wherein at least one of the two half-shells is at least partially transparent, such that the payload is visible there-through.

16. The medical device of claim 14, wherein:
at least one of the two half-shells include a payload channel that extends from the opening and that is configured to receive the distal tip portion; and
the payload is positioned in the payload channel.

17. The medical device of claim 13, wherein:
the payload includes a plurality of individual capsules; and
each of the plurality of individual capsules has a spherical or ovoid shape.

18. The medical device of claim 13, wherein the distal tip portion is a separate piece from the shaft portion, and wherein the distal tip portion is configured to couple with a distal end of the shaft portion via a coupling member.

19. The medical device of claim 13, wherein the deployment mechanism includes a pull wire and a plunger positioned at a distal tip of the pull wire.

20. The medical device of claim 13, wherein an inner surface of the payload chamber defines a plurality of circumferential ribs that extend into the payload chamber.

* * * * *